United States Patent
deLong et al.

(10) Patent No.: US 6,444,840 B1
(45) Date of Patent: Sep. 3, 2002

(54) $C_{11}$ OXYMYL AND HYDROXYLAMINO PROSTAGLANDINS USEFUL AS FP AGONISTS

(75) Inventors: Mitchell Anthony deLong, West Chester; Jack Snyder Amburgey, Jr., Loveland; John August Wos; Biswanath De, both of Cincinnati; David Lindsey Soper, Monroe, all of OH (US)

(73) Assignee: The Procter & Gamble Co., Cincinnati, OH (US)

( * ) Notice: Subject to any disclaimer, the term of this patent is extended or adjusted under 35 U.S.C. 154(b) by 0 days.

(21) Appl. No.: 09/647,380

(22) PCT Filed: Mar. 22, 1999

(86) PCT No.: PCT/IB99/00480

§ 371 (c)(1),
(2), (4) Date: Sep. 28, 2000

(87) PCT Pub. No.: WO99/50242

PCT Pub. Date: Oct. 7, 1999

Related U.S. Application Data

(60) Provisional application No. 60/080,025, filed on Mar. 31, 1998.

(51) Int. Cl.[7] ....................... C07C 69/74; A61K 31/215
(52) U.S. Cl. ....................... 560/121; 514/381; 514/438; 514/460; 514/530; 514/573; 548/251; 548/252; 548/254; 549/76; 549/494; 549/495; 562/503
(58) Field of Search ........................... 562/503; 514/573, 514/530, 438, 461, 381; 560/121; 549/76, 494, 495; 548/251, 252, 254

(56) References Cited

U.S. PATENT DOCUMENTS

| 3,776,938 A | 12/1973 | Bergstrom et al. |
| 4,011,262 A | 3/1977 | Hess et al. |
| 4,024,179 A | 5/1977 | Bindra et al. |
| 4,128,720 A | 12/1978 | Hayashi et al |

FOREIGN PATENT DOCUMENTS

| DE | 001801750 | 7/1969 |
| DE | 002460990 | 7/1976 |
| JP | 02 022226 | 1/1990 |
| WO | WO 90/02253 | 3/1990 |

OTHER PUBLICATIONS

P.W. Collins, et al., "Synthesis of Therapeutically Useful Prostaglandin and Prostacyclin Analogs", *Chem. Rev.*, vol.93, pp. 1533–1564, (1993).

G.L. Bundy, et al., "Synthesis of 17–Phenyl–18, 19, 20–Trinorprostaglandins: 1 The PG Series", *Prostaglandins*, vol. 9, No. 1, pp. 1–4, (1975).

W. Bartman, et al., "Leutolytic Prostaglandins Synthesis and Biological Activity", *Prostaglandins*, vol. 17, No. 2, pp. 301–311, 1979.

C. Liljebris, et al., "Derivatives of 17–Phenyl–18, 19, 20–Trinoprostaglandins $F_{2\alpha}$ Isopropyl Ester: Potential Antiglaucoma Agents", *J. Med. Chem.*, vol. 38, No. 2, pp. 289–304, (1995).

F.A. Fitzpatrick, "Separation of Prostaglandins and Thromboxanes by Gas Chromatography with Glass Capillary Columns", *Analytical Chemistry*, vol. 50, No. 1, pp. 47–52, (1978).

K.A. Waddell, et al., "Combined Capillary Column Gas Chromatography Negative Ion Chemical Ionization Mass Spectrometry of Prostanoids", *Biomed. Mass Spectrom.*, vol. 10, No. 2, pp. 83–88, (1983).

Primary Examiner—Shailendra Kumar
(74) Attorney, Agent, or Firm—David V. Upite; James C. Kellerman; Carl J. Roof

(57) ABSTRACT

The invention provides novel prostaglandin analogs. In particular, the present invention relates to compounds having a structure according to formula (I) wherein $R_1$, $R_2$, $R_3$, $R_4$, $R_5$, $R_6$, W, X, Z, a, b, p and q are defined below. This invention also includes optical isomers, diastereomers and enantiomers of formula (I), and pharmaceutically-acceptable salts, biohydrolyzable amides, esters, and imides thereof. The compounds of the present invention are useful for the treatment of a variety of diseases and conditions, such as bone disorders and glaucoma. Accordingly, the invention further provides pharmaceutical compositions comprising these compounds. The invention still further provides methods of treatment for bone disorders and glaucoma using these compounds or the compositions containing them.

(I)

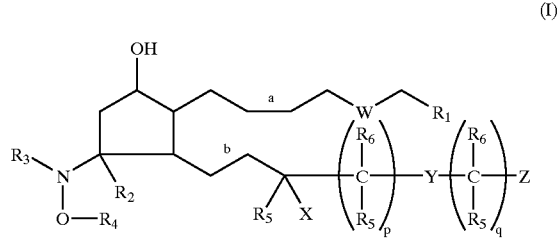

27 Claims, No Drawings

$C_{11}$ OXYMYL AND HYDROXYLAMINO PROSTAGLANDINS USEFUL AS FP AGONISTS

This application is a 371 of PCT/IB99/00498, filed Mar. 22, 1999 which claims benefit of 60/080,075, filed Mar. 31, 1998.

TECHNICAL FIELD

The subject invention relates to certain novel analogs of the naturally occurring prostaglandins. Specifically, the subject invention relates to novel Prostaglandin F analogs. The subject invention further relates to methods of using said novel Prostaglandin F analogs. Preferred uses include methods of treating bone disorders and glaucoma.

BACKGROUND OF THE INVENTION

Naturally occurring prostaglandins (PGA, PGB, PGE, PGF, and PGI) are C-20 unsaturated fatty acids. $PGF_{2\alpha}$, the naturally occurring Prostaglandin F in humans, is characterized by hydroxyl groups at the $C_9$ and $C_{11}$ positions on the alicyclic ring, a cis-double bond between $C_5$ and $C_6$, and a trans-double bond between $C_{13}$ and $C_{14}$. Thus $PGF_{2\alpha}$ has the following formula:

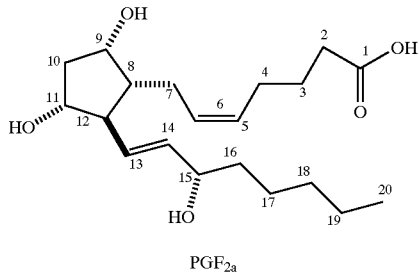

$PGF_{2a}$

Analogs of naturally occurring Prostaglandin F have been disclosed in the art. For example, see U.S. Pat. No. 4,024,179 issued to Bindra and Johnson on May 17, 1977; German Pat. No. DT-002,460,990 issued to Beck, Lerch, Seeger, and Teufel published on Jul. 1, 1976; U.S. Pat. No. 4,128,720 issued to Hayashi, Kori, and Miyake on Dec. 5, 1978; U.S. Pat. No. 4,011,262 issued to Hess, Johnson, Bindra, and Schaaf on Mar. 8, 1977; U.S. Pat. No. 3,776,938 issued to Bergstrom and Sjovall on Dec. 4, 1973; P. W. Collins and S. W. Djuric, "Synthesis of Therapeutically Useful Prostaglandin and Prostacyclin Analogs", *Chem. Rev.* Vol. 93 (1993), pp. 1533–1564; G. L. Bundy and F. H. Lincoln, "Synthesis of 17-Phenyl-18,19,20-Trinorprostaglandins: I. The $PG_1$ Series", *Prostaglandins*, Vol. 9 No. 1 (1975), pp. 1–4; W. Bartman, G. Beck, U. Lerch, H. Teufel, and B. Scholkens, "Luteolytic Prostaglandins: Synthesis and Biological Activity", *Prostaglandins*, Vol. 17 No. 2 (1979), pp. 301–311; C. liljebris, G. Selen, B. Resul, J. Stemschantz, and U. Hacksell, "Derivatives of 17- Phenyl-18,19,20-trinorprostaglandin $F_2\alpha$ Isopropyl Ester: Potential Antiglaucoma Agents", *Journal of Medicinal Chemistry*, Vol. 38 No. 2 (1995), pp. 289–304.

Naturally occurring prostaglandins are known to possess a wide range of pharmacological properties. For example, prostaglandins have been shown to: relax smooth muscle, which results in vasodilatation and bronchodilatation, to inhibit gastric acid secretion, to inhibit platelet aggregation, to reduce intraocular pressure, and to induce labor. Although naturally occurring prostaglandins are characterized by their activity against a particular prostaglandin receptor, they generally are not specific for any one prostaglandin receptor. Therefore, naturally-occurring prostaglandins are known to cause side effects such as inflammation, as well as surface irritation when administered systemically. It is generally believed that the rapid metabolism of the naturally occurring prostaglandins following their release in the body limits the effects of the prostaglandin to a local area. This effectively prevents the prostaglandin from stimulating prostaglandin receptors throughout the body and causing the effects seen with the systemic administration of naturally occurring prostaglandins.

Prostaglandins, especially prostaglandins of the E series (PGE), are known to be potent stimulators of bone resorption. $PGF_{2a}$ has also been shown to be a stimulator of bone resorption but not as potent as $PGE_2$. Also, it has been demonstrated that $PGF_{2a}$ has little effect on bone formation as compared to $PGE_2$. It has been suggested that some of the effects of $PGF_{2a}$ on bone resorption, formation and cell replication may be mediated by an increase in endogenous $PGE_2$ production.

In view of both the wide range of pharmacological properties of naturally occurring prostaglandins and of the side effects seen with the systemic administration of these naturally occurring prostaglandins, attempts have been made to prepare analogs to the naturally occurring prostaglandins that are selective for a specific receptor or receptors. A number of such analogs have been disclosed in the art. Though a variety of prostaglandin analogs have been disclosed, there is a continuing need for potent, selective prostaglandin analogs for the treatment of a variety diseases and conditions.

SUMMARY OF THE INVENTION

The invention provides novel PGF analogs. In particular, the present invention relates to compounds having a structure according to the following formula:

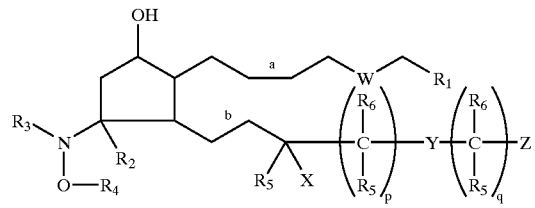

wherein $R_1$, $R_2$, $R_3$, $R_4$, $R_5$, R6, W, X, Z, a, b, p, and q are defined below.

This invention also includes optical isomers, diastereomers and enantiomers of the formula above, and pharmaceutically-acceptable salts, biohydrolyzable amides, esters, and imides thereof.

The compounds of the present invention are useful for the treatment of a variety of diseases and conditions, such as bone disorders and glaucoma. Accordingly, the invention further provides pharmaceutical compositions comprising these compounds. The invention still further provides methods of treatment for bone disorders and glaucoma using theses compounds or the compositions containing them.

DETAILED DESCRIPTION OF THE INVENTION

Terms and Definitions

"Acyl" is a group suitable for acylating a nitrogen atom to form an amide or carbamate or an oxygen atom to form an ester group. Preferred acyl groups include benzoyl, acetyl, tert-butyl acetyl, para-phenyl benzoyl, and trifluoroacetyl. More preferred acyl groups include acetyl and benzoyl. The most preferred acyl group is acetyl.

"Alkyl" is a saturated or unsaturated hydrocarbon chain having 1 to 18 carbon atoms, preferably 1 to 12, more preferably 1 to 6, more preferably still 1 to 4 carbon atoms. Alkyl chains may be straight or branched. Preferred branched alkyl have one or two branches, preferably one branch. Preferred alkyl are saturated. Unsaturated alkyl have one or more double bonds and/or one or more triple bonds. Preferred unsaturated alkyl have one or two double bonds or one triple bond, more preferably one double bond. Alkyl chains may be unsubstituted or substituted with from 1 to 4 substituents. Preferred substituted alkyl are mono-, di-, or trisubstituted. The substituents may be lower alkyl, halo, hydroxy, aryloxy (e.g., phenoxy), acyloxy (e.g., acetoxy), carboxy, monocyclic aromatic ring (e.g., phenyl), monocyclic heteroaromatic ring, monocyclic carbocyclic aliphatic ring, monocyclic heterocyclic aliphatic ring, and amino.

"Lower alkyl" is an alkyl chain comprised of 1 to 6, preferably 1 to 4 carbon atoms.

"Aromatic ring" is an aromatic hydrocarbon ring system. Aromatic rings are monocyclic or fused bicyclic ring systems. Monocyclic aromatic rings contain from about 5 to about 10 carbon atoms, preferably from 5 to 7 carbon atoms, and most preferably from 5 to 6 carbon atoms in the ring. Bicyclic aromatic rings contain from 8 to 12 carbon atoms, preferably 9 or 10 carbon atoms in the ring. Aromatic rings may be unsubstituted or substituted with from 1 to 4 substituents on the ring. The substituents may be halo, cyano, alkyl, heteroalkyl, haloalkyl, phenyl, phenoxy or any combination thereof. Preferred substituents include halo and haloalkyl. Preferred aromatic rings include naphthyl and phenyl. The most preferred aromatic ring is phenyl.

"Bone disorder" means the need for bone repair or replacement. Conditions in which the need for bone repair or replacement may arise include: osteoporosis (including post menopausal osteoporosis, male and female senile osteoporosis and corticosteroid induced osteoporosis), osteoarthritis, Paget's disease, osteomalacia, multiple myeloma and other forms of cancer, prolonged bed rest, chronic disuse of a limb, anorexia, microgravity, exogenous and endogenous gonadal insufficiency, bone fracture, non-union, defect, prosthesis implantation and the like.

"Carbocyclic aliphatic ring" is a saturated or unsaturated hydrocarbon ring. Carbocyclic aliphatic rings are not aromatic. Carbocyclic aliphatic rings are monocyclic, or are fused, Spiro, or bridged bicyclic ring systems. Monocyclic carbocyclic aliphatic rings contain from about 4 to about 10 carbon atoms, preferably from 4 to 7 carbon atoms, and most preferably from 5 to 6 carbon atoms in the ring. Bicyclic carbocyclic aliphatic rings contain from 8 to 12 carbon atoms, preferably from 9 to 10 carbon atoms in the ring. Carbocyclic aliphatic rings may be unsubstituted or substituted with from 1 to 4 substituents on the ring. The substituents may be halo, cyano, alkyl, heteroalkyl, haloalkyl, phenyl, phenoxy or any combination thereof. Preferred substituents include halo and haloalkyl. Preferred carbocyclic aliphatic rings include cyclopentyl, cyclohexyl, cyclohexenyl, cycloheptyl, and cyclooctyl. More preferred carbocyclic aliphatic rings include cyclohexyl, cycloheptyl, and cyclooctyl.

"Halo" is fluoro, chloro, bromo or iodo. Preferred halo are fluoro, chloro and bromo; more preferred are chloro and fluoro, especially fluoro.

"Haloalkyl" is a straight, branched, or cyclic hydrocarbon substituted with one or more halo substituents. Preferred haloalkyl are $C_1$–$C_{12}$; more preferred are $C_1$–$C_6$; more preferred still are $C_1$–$C_3$. Preferred halo substituents are fluoro and chloro. The most preferred haloalkyl is trifluoromethyl.

"Heteroalkyl" is a saturated or unsaturated chain containing carbon and at least one heteroatom, wherein no two heteroatoms are adjacent. Heteroalkyl chains contain from 1 to 18 member atoms (carbon and heteroatoms) in the chain, preferably 1 to 12, more preferably I to 6, more preferably still 1 to 4. Heteroalkyl chains may be straight or branched. Preferred branched heteroalkyl have one or two branches, preferably one branch. Preferred heteroalkyl are saturated. Unsaturated heteroalkyl have one or more double bonds and/or one or more triple bonds. Preferred unsaturated heteroalkyl have one or two double bonds or one triple bond, more preferably one double bond. Heteroalkyl chains may be unsubstituted or substituted with from 1 to 4 substituents. Preferred substituted heteroalkyl are mono-, di-, or trisubstituted. The substituents may be lower alkyl, halo, hydroxy, aryloxy (e.g., phenoxy), acyloxy (e.g., acetoxy), carboxy, monocyclic aromatic ring (e.g., phenyl), monocyclic heteroaromatic ring, monocyclic carbocyclic aliphatic ring, monocyclic heterocyclic aliphatic ring, and amino.

"Heteroaromatic ring" is an aromatic ring system containing carbon and from 1 to about 4 heteroatoms in the ring. Heteroaromatic rings are monocyclic or fused bicyclic ring systems. Monocyclic heteroaromatic rings contain from about 5 to about 10 member atoms (carbon and heteroatoms), preferably from 5 to 7, and most preferably from 5 to 6 in the ring. Bicyclic heteroaromatic rings contain from 8 to 12 member atoms, preferably 9 or 10 in the ring. Heteroaromatic rings may be unsubstituted or substituted with from 1 to 4 substituents on the ring. The substituents may be halo, cyano, alkyl, heteroalkyl, haloalkyl, phenyl, phenoxy or any combination thereof. Preferred substituents include halo, haloalkyl, and phenyl. Preferred heteroaromatic rings include thienyl, thiazolo, purinyl, pyrimidyl, pyridyl, and furanyl. More preferred heteroaromatic rings include thienyl, furanyl, and pyridyl. The most preferred heteroaromatic ring is thienyl.

"Heteroatom" is a nitrogen, sulfur, or oxygen atom. Groups containing more than one heteroatom may contain different heteroatoms.

"Heterocyclic aliphatic ring" is a saturated or unsaturated ring containing carbon and from 1 to about 4 heteroatoms in the ring, wherein no two heteroatoms are adjacent in the ring and no carbon in the ring that has a heteroatom attached to it also has a hydroxyl, amino, or thiol group attached to it. Heterocyclic aliphatic rings are not aromatic. Heterocyclic aliphatic rings are monocyclic, or are fused or bridged bicyclic ring systems. Monocyclic heterocyclic aliphatic rings contain from about 4 to about 10 member atoms (carbon and heteroatoms), preferably from 4 to 7, and most preferably from 5 to 6 in the ring. Bicyclic heterocyclic aliphatic rings contain from 8 to 12 member atoms, preferably 9 or 10 in the ring. Heterocyclic aliphatic rings may be unsubstituted or substituted with from 1 to 4 substituents on the ring. The substituents may be halo, cyano, alkyl, heteroalkyl, haloalkyl, phenyl, phenoxy or any combination thereof. Preferred substituents include halo and haloalkyl. Preferred heterocyclic aliphatic rings include piperzyl, morpholinyl, tetrahydrofuranyl, tetrahydropyranyl and piperdyl.

"Phenyl" is a monocyclic aromatic ring which may or may not be substituted with from about 1 to about 4 substituents. The substituents may be fused but not bridged and may be substituted at the ortho, meta or para position on the phenyl ring, or any combination thereof. The substituents may be halo, cyano, alkyl, heteroalkyl, haloalkyl, phenyl, phenoxy or any combination thereof. Preferred substituents on the phenyl ring include halo and haloalkyl. The most preferred substituent is halo. The preferred substitution pattern on the phenyl ring is ortho or meta. The most preferred substitution pattern on the phenyl ring is meta.

Compounds

The subject invention involves compounds having the following structure:

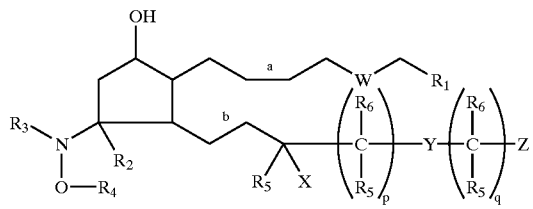

In the above structure, $R_1$ is $CO_2H$, $C(O)NHOH$, $CO_2R_7$, $CH_2OH$, $S(O)_2R_7$, $C(O)NHR_7$, $C(O)NHS(O)_2R_7$, or tetrazole; wherein $R_7$ is alkyl, heteroalkyl, monocyclic carbocyclic aliphatic ring, monocyclic heterocyclic aliphatic ring, monocyclic aromatic ring, or monocyclic heteroaromatic ring. Preferred $R_7$ is methyl, ethyl, and isopropyl. Preferred $R_7$ is $CO_2H$, $C(O)NHOH$, $CO_2R_7$ $C(O)NHS(O)_2R_7$, and tetrazole. Most preferred $R_1$ is $CO_2H$ and $CO_2R_7$.

In the above structure, W is O, NH, S, S(O), S(O)$_2$, or (CH$_2$)$_m$; wherein m is an integer from 0 to about 3. Preferred W is O and (CH$_2$)$_m$. Most preferred W is (CH$_2$)$_1$.

In the above structure, $R_2$ is H and $R_3$ is H or lower alkyl, or $R_2$ and $R_3$ together form a covalent bond.

In the above structure, $R_4$ is H, alkyl, heteroalkyl, monocyclic carbocyclic aliphatic ring, monocyclic heterocyclic aliphatic ring, monocyclic aromatic ring, or monocyclic heteroaromatic ring. Preferred $R_4$ is H and lower alkyl. Most preferred $R_4$ is H.

In the above structure, each $R_5$ is independently selected from the group consisting of H, CH$_3$, and C$_2$H$_5$. Preferred $R_5$ is H and CH$_3$. Most preferred $R_5$ is H.

In the above structure, X is NHR$_8$ or OR$_8$, wherein each $R_8$ is independently selected from the group consisting of H, acyl, alkyl, heteroalkyl, monocyclic carbocyclic aliphatic ring, monocyclic heterocyclic aliphatic ring, monocyclic aromatic ring, and monocyclic heteroaromatic ring. Preferred $R_8$ is H. Preferred X is OR$_8$. Most preferred X is OH.

In the above structure, each R6 is independently selected from the group consisting of H, CH$_3$, C$_2$H$_5$, OR$_8$, NHR$_8$. Preferred $R_6$ is H, CH$_3$, C$_2$H$_5$, OR$_8$. Most preferred $R_6$ is H and CH$_3$.

In the above structure, Y is O, NHR$_8$, S, S(O), or S(O)$_2$, provided no carbon has more than one heteroatom attached to it. Preferred Y is O, NHR$_8$, and S. Most preferred Y is O.

In the above structure, Z is H, methyl, monocyclic carbocyclic aliphatic ring, monocyclic heterocyclic aliphatic ring, monocyclic aromatic ring, or monocyclic heteroaromatic ring, bicyclic carbocyclic aliphatic ring, bicyclic heterocyclic aliphatic ring, bicyclic aromatic ring, or bicyclic heteroaromatic ring, provided that when Y is S, S(O), or S(O)$_2$ and Z is H, q is at least 1. Preferred Z is monocyclic aromatic ring and monocyclic heteroaromatic ring. More preferred Z is thienyl and phenyl.

In the above structure, a and b are independently selected from the group consisting of single bond, cis double bond, and trans double bond. Preferred a is single bond or cis double bond, and preferred b is single bond or trans double bond.

In the above structure, p is an integer from 1 to 5, q is an integer from 0 to 5, and p+qis 1 to 5.

The invention also includes optical isomers, diastereomers and enantiomers of the above structure. Preferred stereochemistry at all stereocenters of the compounds of the invention mimic that of naturally occurring PGF$_{2\alpha}$.

It has been discovered that the novel PGF analogs of the subject invention are useful for treating bone disorders, especially those that require a significant increase in bone mass, bone volume, or bone strength. Surprisingly, the compounds of the subject invention have been found to provide the following advantages over known bone disorder therapies: (1) An increase trabecular number through formation of new trabeculae; (2) An increase in bone mass and bone volume while maintaining a more normal bone turn-over rate; and/or (3) An increase in bone formation at the endosteal surface without increasing cortical porosity.

In order to determine and assess pharmacological activity, testing of the subject compounds in animals is carried out using various assays known to those skilled in the art. For example, the bone activity of the subject compounds can be conveniently demonstrated using an assay designed to test the ability of the subject compounds to increase bone volume, mass, or density. An example of such assays is the ovariectomized rat assay.

In the ovariectomized rat assay, six-month old rats are ovariectomized, aged 2 months, and then dosed once a day subcutaneously with a test compound. Upon completion of the study, bone mass and/or density can be measured by dual energy x-ray absorptometry (DXA) or peripheral quantitative computed tomography (pQCT), or micro computed tomography (mCT). Alternatively, static and dynamic histomorphometry can be used to measure the increase in bone volume or formation.

Pharmacological activity for glaucoma can be demonstrated using assays designed to test the ability of the subject compounds to decrease intraocular pressure. Examples of such assays are described in the following reference, incorporated herein: C. liljebris, G. Selen, B. Resul, J. Sternschantz, and U. Hacksell, "Derivatives of 17- Phenyl-18,19,20-trinorprostaglandin F$_2\alpha$ Isopropyl Ester: Potential Antiglaucoma Agents", *Journal of Medicinal Chemistry*, Vol. 38 No. 2 (1995), pp. 289–304.

Compounds useful in the subject invention can be made using conventional organic syntheses. Particularly preferred syntheses are the following two general reaction schemes:

Scheme 1
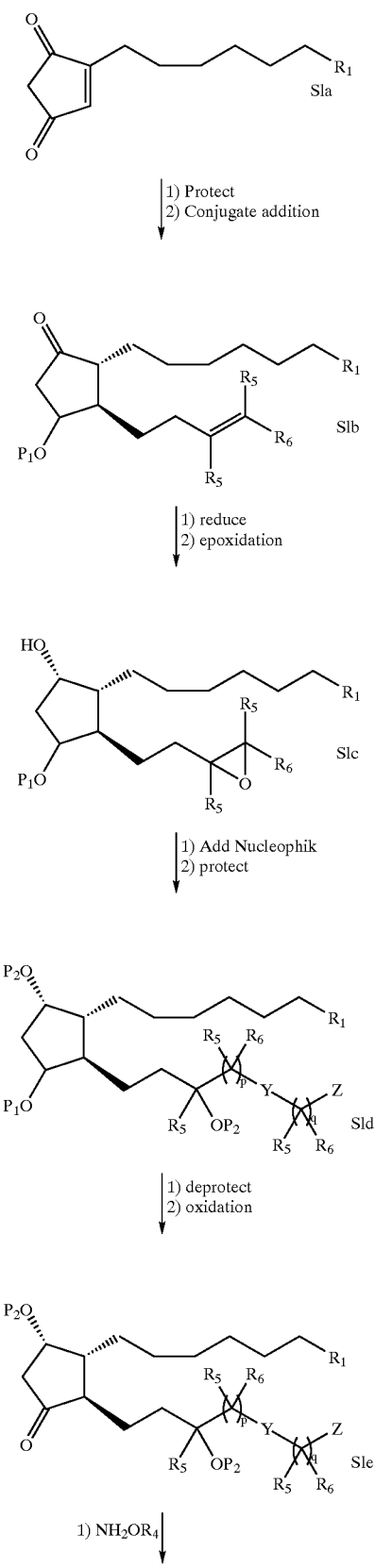
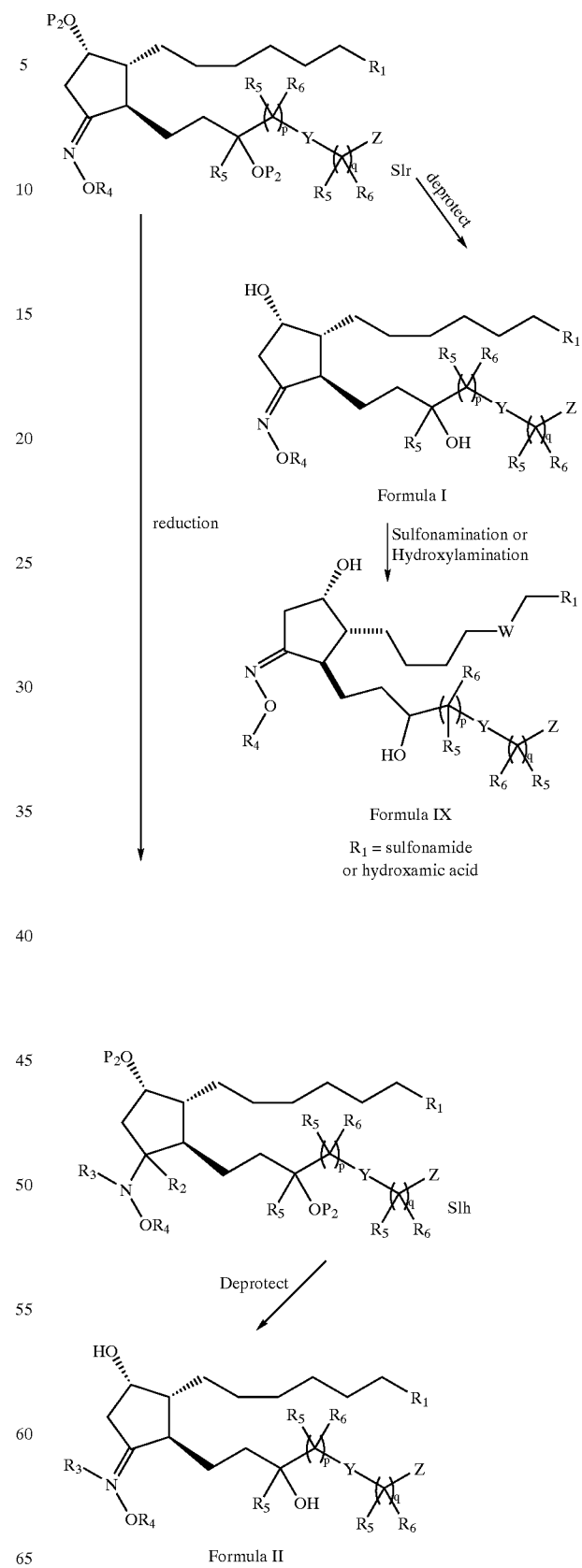
Formula I
Formula IX
$R_1$ = sulfonamide or hydroxamic acid
Formula II In Scheme 1, $R_1$, $R_2$, $R_3$, $R_4$, $R_5$, $R_6$, X, Y, p, q, and Z are as defined above unless otherwise defined. The Methyl 7[3-(R)-hydroxy-5-oxo-1-cyclopent-1-yl] heptanoate (S1a) depicted as starting material for Scheme 1 is commercially available (such as from Sumitomo Chemical or Cayman Chemical).

In the above Scheme 1, Methyl 7-[3-(R)-hydroxy-5-oxo-1-cyclopent-1-yl] heptanoate (S1a) is reacted with a silylating agent and base in a solvent that will allow the silylation to proceed. Preferred silylating agents include tert-butyldimethylsilyl chloride and tert-butyldimethylsilyl trifluoromethanesulphonate. The most preferred silylating agent is tert-butyldimethylsilyl trifluoromethanesulphonate. Preferred bases include triethylamine, trimethylamine, and 2,6-lutidine. More preferred bases include triethylamine and 2,6-lutidine. The most preferred base is 2,6-lutidine. Preferred solvents include halocarbon solvents with dichloromethane being the most preferred solvent. The reaction is allowed to proceed at a temperature preferably between −100° C. and 100° C., more preferably between −80° C. and 80° C., and most preferably between −70° C. and 23° C.

The resulting silylated compound is isolated by methods known to those of ordinary skill in the art. Such methods include, but are not limited to, extraction, solvent evaporation, distillation, and crystallization. Preferably, the silyl ether is purified after isolation by distillation under vacuum.

The silylated compound is then reacted with the cuprate generated via Grignard formation of the appropriate alkenyl bromide as disclosed, for example, in the following references: H.O. House et. al., "The Chemistry of Carbanions: A Convenient Precursor for the Generation of Lithium Organocuprates", *J. Org. Chem.* Vol. 40 (1975) pp. 1460–69; and P. Knochel et. al., "Zinc and Copper Carbenoids as Efficient and Selective a'/d' Multicoupling Reagents", *J. Amer. Chem. Soc.* Vol. 111 (1989) p. 6474–76. Preferred alkenyl bromides include 4-bromo-1-butene, 4-bromo-1-butyne, 4-bromo-2-methyl-1-butene, and 4-bromo-2-ethyl-1-butene. The most preferred alkenyl bromide is 4-bromo-1-butene. Preferred solvents include ethereal solvents, of which diethyl ether and tetrahydrofuran are preferred. The most preferred solvent is tetrahydrofuran. The Grignard reagent is allowed to form at a temperature between 100° C. and 23° C., more preferably between 85° C. and 30° C., and most preferably between 75° C. and 65° C. The reaction time is preferably between 1 hour and 6 hours, with a more preferred reaction time being between 2 hours and 5 hours, and the most preferred reaction time being between 3 hours and 4 hours.

Once the Grignard reagent is formed, the cuprate is generated from the alkenyl magnesium species. The temperature range for cuprate formation is between −100° C. and 0° C. The preferred temperature range is between −80° C. and −20° C. The more preferred temperature range is between −75° C. and −50° C. The preferred reaction time is between 30 minutes and 6 hours. The more preferred reaction time is between 45 minutes and 3 hours. The most preferred reaction time is between 1 hour and 1.5 hours.

The compound depicted as S1b is isolated by methods known to one of ordinary skill in the art. Such methods include, but are not limited to, extraction, solvent evaporation, distillation, and crystallization. Preferably, S1b is purified by flash chromatography on silica gel (Merck, 230–400 mesh) using 10% EtOAc/hexanes as the eluent.

S1b is then reacted with a hydride reducing agent and a polar, protic solvent to give the $C_9$ alcohol. Preferred reducing agents include lithium aluminum hydride, sodium borohydride, and L-selectride. More preferred reducing agents include sodium borohydride, and L-selectride. The most preferred reducing agent is sodium borohydride. Preferred solvents include methanol, ethanol, and butanol. The most preferred solvent is methanol. The reduction is carried out at a temperature between −100° C. and 23° C. The preferred temperature range is between −60° C. and 0° C. The most preferred temperature range is between −45° C. and −20° C.

The resulting alcohol of S1b is isolated by methods known to one of ordinary skill in the art. Such methods include, but are not limited to, extraction, solvent evaporation, distillation, and crystallization. Preferably, the alcohol is purified by flash chromatography on silica gel (Merck, 230–400 mesh) using 20% EtOAc/hexanes as the eluent.

The alcohol can be protected as described previously herein. The protected or unprotected alcohol is then treated with meta-chloroperbenzoic acid in a halocarbon solvent to provide the novel epoxide intermediate depicted as S1c. Preferred halocarbon solvents include dichloromethane, dichloroethane, and chloroform. More preferred halocarbon solvents are dichloromethane and dichloroethane. The most preferred halocarbon solvent is dichloromethane.

The compound depicted as S1c is isolated by methods known to one of ordinary skill in the art. Such methods include, but are not limited to, extraction, solvent evaporation, distillation, and crystallization. Preferably, S1c is purified by flash chromatography on silica gel (Merck, 230–400 mesh) using 20% EtOAc/hexanes as the eluent.

The intermediate epoxide depicted as S1c can be reacted with a variety of oxygen, sulfur and nitrogen containing nucleophiles as disclosed, for example, in J. G. Smith, "Synthetically Useful Reactants of Epoxides", *Synthesis* (1984) p. 629–656, to provide the $C_{11}$-protected 13,14-dihydro-15-substituted-16-tetranor prostaglandin $F_1\alpha$ derivatives.

With sulfur nucleophiles, the reaction is carried out preferably between 150° C. and 0° C., more preferably between 120° C. and 20° C., and most preferably between 80° C. and 50° C. Preferred bases for the reaction include triethylamine, N.N diisopropylethylamine, and trimethylamine. The most preferred base is triethylamine. Preferred solvents for the reaction are aromatic hydrocarbon solvents. Preferred solvents include xylenes, toluene, and benzene. The most preferred solvent is benzene. With nitrogen and oxygen nucleophiles, preferred solvents include ethereal solvents and polar, protic solvents. More preferred ethereal solvents include diethyl ether, dibutyl ether and tetrahydrofuran. The most preferred ethereal solvent is tetrahydrofuran. More preferred polar, protic solvents include ethyl alcohol, methyl alcohol, and tert-butyl alcohol. The most preferred polar, protic solvent is ethyl alcohol.

The ring-opening process with nitrogen and oxygen nucleophiles can be catalyzed with Lewis acids. Preferred Lewis acids include magnesium perchlorate, trimethylsilyl trifluoromethanesulphonate, and trimethylaluminum. The most preferred Lewis acid is magnesium perchlorate. The reaction is carried out at a temperature between 150° C. and 23° C., preferably between 125° C. and 40° C., and more preferably between 100° C. and 75° C.

The selective protection of C-9 and C-15 can be accomplished by methods known to one of ordinary skill in the art. Preferred protecting groups include, but are not limited to acylating agents, alkylating agent, and carbonate forming agents. The most preferred protecting group is acetyl. Preferred solvents include halohydrocarbon and amine solvents.

The most preferred is pyridine. Preferred reagents include acetyl halides and acetic anhydride. The most preferred is acetic anhydride. The temperature range for the reaction is −100° C. to 100° C. The preferred range is −10° C. to 40° C. More preferred range is −5° C. to 30° C. The preferred reaction time is 1 hour to 48 hours. More preferred is 6 hours to 24 hours.

The compound depicted as S1d is isolated by methods known to one of ordinary skill in the art. Such methods include, but are not limited to, extraction, solvent evaporation, distillation, and crystallization. Preferably, S1d is purified by flash chromatography on silica gel (Merck, 230–400 mesh) using 10% EtOAc/hexanes as the eluent.

The resulting C-11 ether on compound S1d is deprotected using using a fluoride equivalent. The deprotection reagents include tetrabutyl ammonium fluoride, hydrogen fluoride in pyridine, potassium fluoride, and treatment with strong acid. Preferred is HF/pyridine. The temperature range is −100° C. to 50° C. The preferred temperature range is −50° C. to 30° C. The most preferred is −20° C. to 10° C. The preferred solvents are THF, Acetonitrile, and Et$_2$O. Most preferred is acetonitrile.

The compound is isolated by methods known to one of ordinary skill in the art. Such methods include, but are not limited to, extraction, solvent evaporation, distillation, and crystallization. Preferably the compound is purified by flash chromatography on silica gel (Merck, 230–400 mesh) using 20% EtOAc/hexanes as the eluent.

Compound S1e is produced by the oxidation of the C-11 alcohol to give the ketone. The oxidation can be accomplished by, but are not limited to, Swern, Jones, PCC, PDC. The most preferred is PCC. The most preferred solvent is dichloromethane. The preferred reaction temperature is −30° C. to 100° C. The most preferred is 0° C. to 50° C. Compound S1e is isolated by methods known to one of ordinary skill in the art. Such methods include, but are not limited to, extraction, solvent evaporation, distillation, and crystallization. Preferably the compound is purified by filtering through Florcil and solvent evaporation.

Compound S1f is formed by the reaction of $NH_2OR_4$ in buffered solution of solvents. The preferred buffer is sodium acetate. The preferred solvent ratio is 3:1:1 (methanol:dioxane:water). The preferred temperature range is −20° C. to 100° C. The compound depicted as S1f is isolated by methods known to one of ordinary skill in the art. Such methods include, but are not limited to, extraction, solvent evaporation, distillation, and crystallization. Preferably, S1f is purified by flash chromatography on silica gel (Merck, 230–400 mesh) using 10% EtOAc/hexanes as the eluent.

Deprotection of S1f is accomplished by methods known to one of ordinary skill in the art and yields compounds of Formula I. Compounds depicted by Formula I are exemplified in Examples 1–15.

Reduction of the oxime of S1f gives the compound S1h as the hydroxyl amine. The reduction is accomplished by treatment with sodium cyanoborohydride. The preferred solvent is MeOH. The preferred temperature range is −100° C. to 100° C.

Deprotection of S1h is accomplished by methods known to one of ordinary skill in the art and yields compounds of Formula II. Compounds depicted by Formula II are exemplified in Examples 29–34.

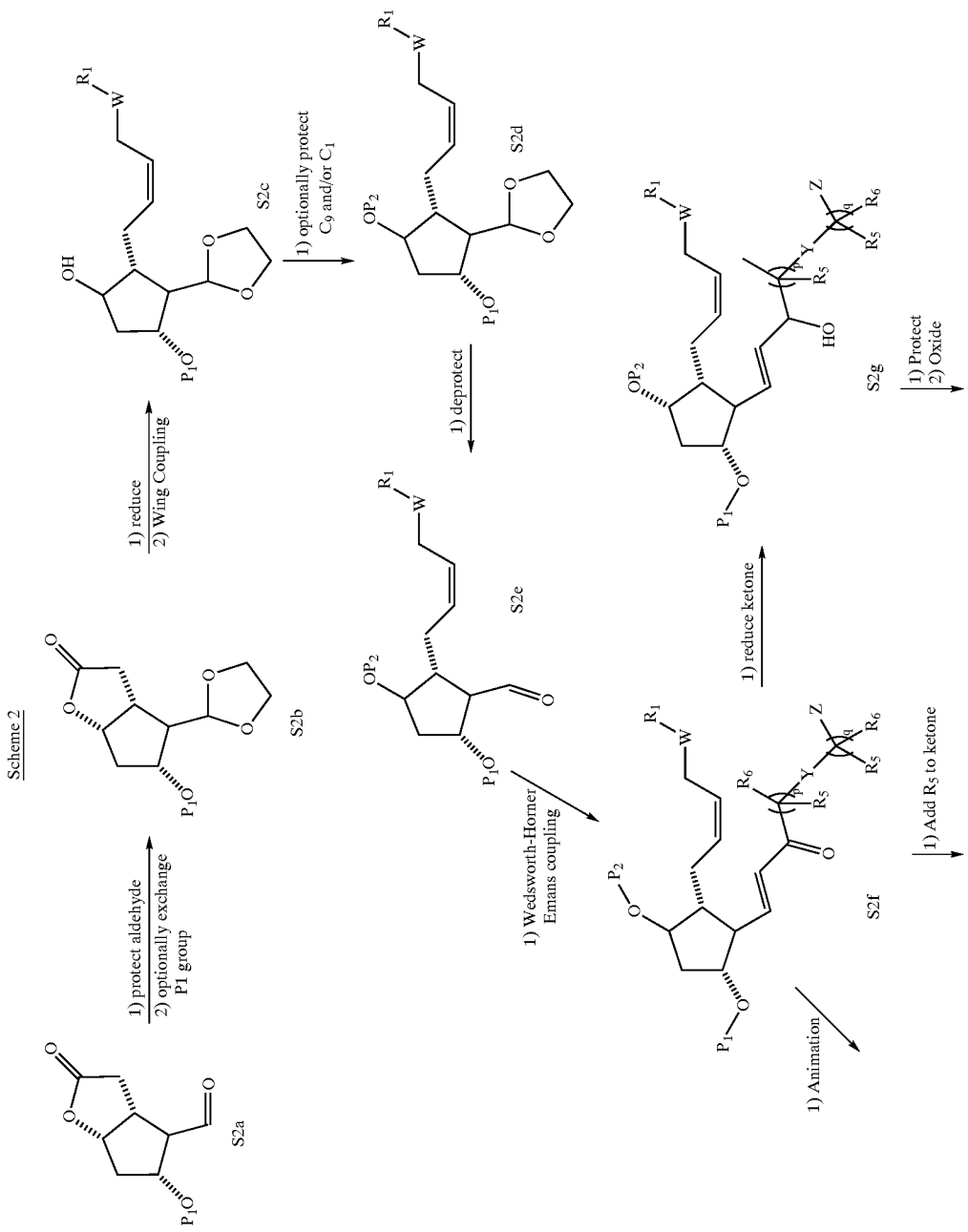

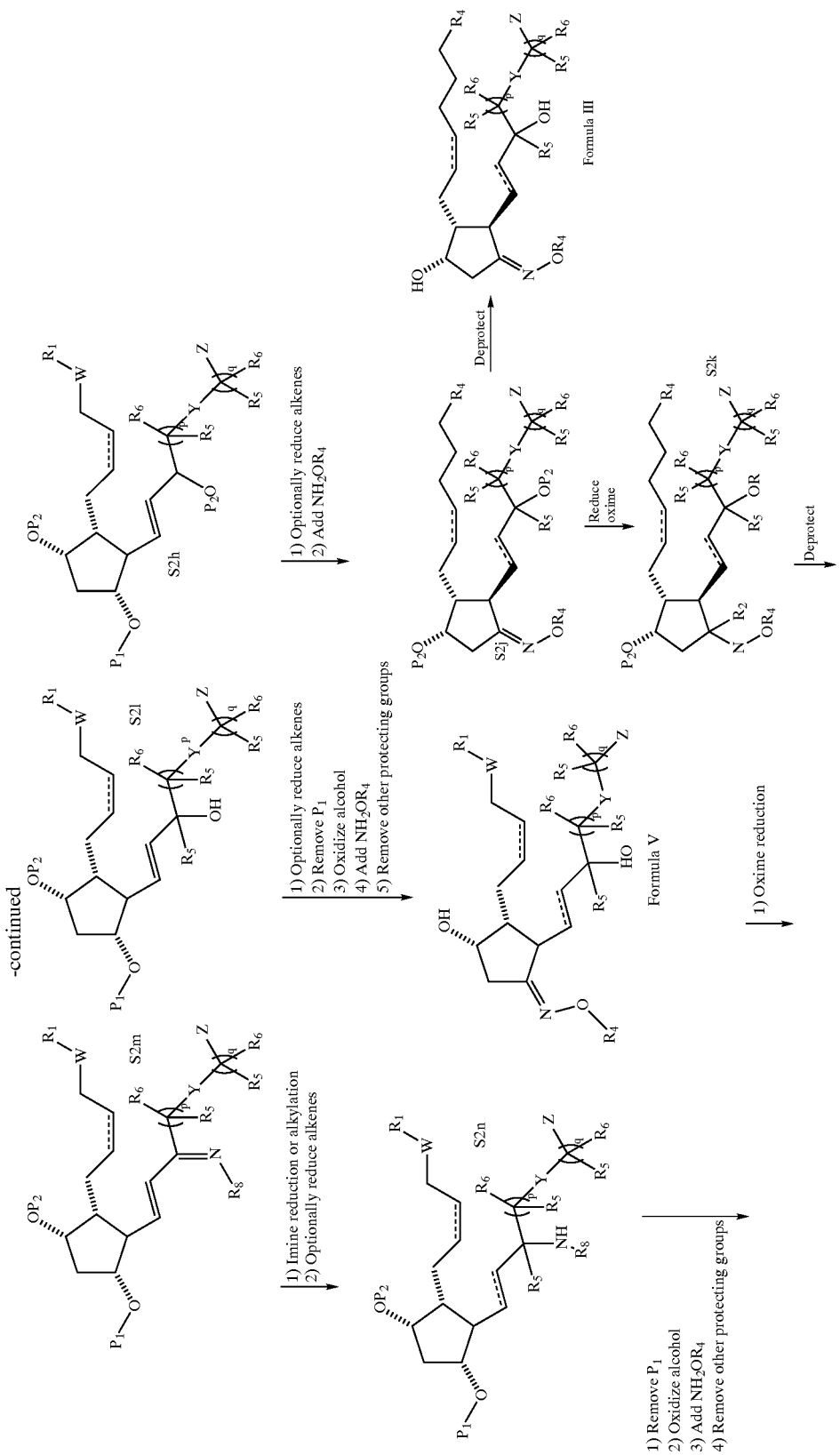

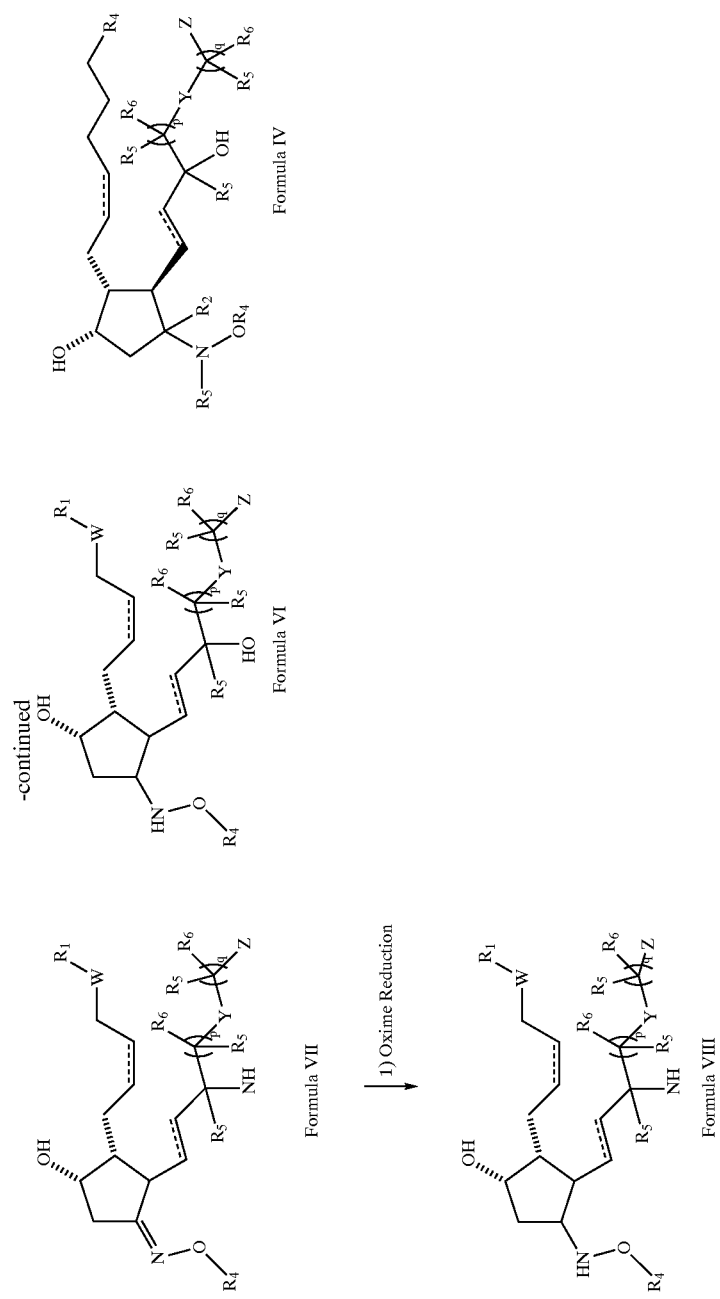

In Scheme 2, $R_1$, $R_2$, $R_3$, $R_4$, $R_5$, $R_6$ W, X, Z, and P are as defined above unless otherwise defined. The Corey Aldehyde (S2a) depicted as starting material for Scheme 2 is commercially available (such as from Aldrich Chemical or Cayman Chemical).

In the above Scheme 2, Corey Aldehyde is commercially-available with either a silyl group ($P_1$) or an ester group ($P_1$) attached to the alcohol. The preferred protecting groups include tert-butyldimethylsilyl, acetate, benzoate, and para-phenyl benzoate. The most preferred protecting group is tert-butyldimethylsilyl.

The Corey aldehyde (S2a) is first reacted with an aldehyde protecting group to make a ketal or acetal. Examples of this type of protection are found in Greene and Wuts, *Protecting Groups in Organic Synthesis*, 2d ed., Wiley & Sons, N.Y. 1991. In this case, especially preferred are cyclic ketals and acetals. The aldehyde (S2a) is reacted with the appropriate 1,2- diol and a suitable acidic catalyst. The solvent can be the diol, and an anhydrous solvent, such as ether or dichloromethane. Particularly useful is 1,2-bis-TMS ethylene glycol to effect this transformation in ether at room temperature.

The ketal-protected S2a may then undergo a routine of protection/deprotection if desired, to exchange the $P_1$ group for a more suitable one, using procedures known in the art. Particularly useful is the exchange of a silyl group for an acyl group, and vice versa. Also useful is the exchange of a silyl or acyl group for an o-bromo-benzyl ether group.

The compound (S2b) is then subjected to a DIBAL reduction to make the hemiacetal. This intermediate is not isolated but reacted as soon as possible with a Wittig salt to form an alkene (S2c). Particularly preferred Wittig salts are derived from omega bromo- four to five carbon straight chain carboxylic acids and 3-oxocarboxylic acids. These are conveniently combined with triphenylphosphine in a suitable solvent to form the reactive Wittig salts. Other preferred reagents include straight chain omega-bromo tetrazoles and primary nitriles.

The compound (S2c) is not isolated, but reacted crude with diazomethane in diethyl ether or, preferably, with TMS diazomethane in methanol to give S2d. In addition, a suitable protecting group may be placed on the $C_9$ alcohol at this time. The compound S2d is isolated by methods known to one of ordinary skill in the art. Such methods include, but are not limited to, extraction, solvent evaporation, distillation, and crystallization. Preferably, it is purified by flash chromatography on silica gel (Merck, 230–400 mesh) using 10% EtOAc/hexanes as the eluent.

The compound (S2d) is then optionally reduced at C-5,6 to give the saturated alpha chain of the prostaglandin, if desired, or taken on without reduction. The cyclic ketal is removed with acid or acidic ion exchange resin in a suitable solvent to give the free aldehyde. Preferred solvents include THF/water mixtures.

The resulting aldehyde (S2e) is not isolated but reacted with ketone-stabilized phosphonium salts. These are generally referred to as "Wadsworth-Horner-Erumons" reagents. This reaction requires a mild base. Examples of suitable bases include sodium carbonate or triethyl amine. The product ketone (S2f) is purified by methods known to one of ordinary skill in the art. Such methods include, but are not limited to, extraction, solvent evaporation, distillation, and crystallization. Preferably, the ketone (S2f) is purified by flash chromatography on silica gel (Merck, 230–400 mesh) using 20% EtOAc/hexanes as the eluent.

As seen in Scheme 2 above, the ketone (S2f) can be reacted in three ways. Reduction of the ketone with a reducing agent such as the Luche reagent, effects an alcohol at C-15, as illustrated by S2g.

At this point, the alcohols of S2g at C-9 and C-15 may be protected, if needed or desired. If so, the alcohols can be protected as described previously herein. The S2g compound containing protected or unprotected alcohols is then treated with a deprotecting agent to release selectively $P_1$ on C-11. Examples of such selective deprotection reactions are given in Greene and Wuts.

Alternatively, when $P_1$ is the o-bromobenzyl ether, reduction of the bromine with a radical reducing agent such as $(n-Bu)_3SnH$ will cause the radical-induced oxidation of C-11 to the ketone without needing protection.

Compounds of the type S2h can be converted into compounds of Formula III and Formula IV. Compounds depicted by Formula III are exemplified in Examples 16–28. Compounds depicted by Formula IV are exemplified in Examples 35–40.

The ketone (S2f) can also be converted into compounds of the type S2l. This occurs by the addition of suitable nucleophile to the ketone (S2f). Examples of nucleophiles include methyl magnesium bromide. Using substantially the same techniques described above, the compounds of the type S2l can be converted into compounds of Formula V, and compounds of Formula V can be converted into compounds of Formula VI. Compounds depicted by Formula V are exemplified in Examples 41–43, and compounds depicted by Formula VI are exemplified in Example 44.

Compounds of the type S2f can also be reacted to give compounds of the type S2m by reacting the ketone at C-15 with an active amine. Examples of reactive amines include methyl amine and ethyl amine. The products can be reduced or can react with nucleophiles using standard techniques, and the reduction can also extend to reduce the alkenes, if desired, using a reagent such as hydrogen gas over palladium on carbon. Alternatively, sodium cyanoborohydride will selectivity reduce the imine without disrupting the alkenes. Finally, a suitable nucleophile, preferably such as a methyl cerium reagent, can add to the imine. Addition of the methylcerium nucleophile (~1.5 equiv.) is described in T. Imamoto, et al., "Carbon-Carbon Bond Forming Reactions Using Cerium Metal or Organocerium (III) Reagents", *J. Org. Chem.* Vol. 49 (1984) p. 3904–12; T. Imamoto, et al., "Reactions of Carbonyl Compounds with Grignard Reagents in the Presence of Cerium Chloride", *J. Am. Chem. Soc.* Vol. 111 (1989) p. 4392–98; and references cited therein, gives the aminomethyl derivative. In that case, $R_5$ in compound S1n would be a methyl group.

Using the reactions disclosed above for compounds of the type S2h, compounds of Formula VII can be made from S2n. Compounds depicted by Formula VII are exemplified in Example 45. Compounds of the Formula VIII can thus be made from compounds of Formula VII. Compounds depicted by Formula VII are exemplified in Examples 46.

Compounds of Formula IX can be made from sulfonation or hydroxylamination of compounds of Formula III. Compounds depicted by Formula IX are exemplified in Examples 47–48.

These compounds are isolated by methods known to one of ordinary skill in the art. Such methods include, but are not limited to, extraction, solvent evaporation, distillation, and crystallization.

The following non-limiting examples illustrate the compounds, compositions, and uses of the present invention.

EXAMPLES

Compounds are analyzed using $^1H$ and $^{13}C$ NMR, Elemental analysis, mass spectra, high resolution mass spectra and/or IR spectra as appropriate.

Typically, inert solvents are used, preferably in dried form. For example, tetrahydrofuran (THF) is distilled from sodium and benzophenone, diisopropylamine is distilled from calcium hydride and all other solvents are purchased as the appropriate grade. Chromatography is performed on silica gel (70–230 mesh; Aldrich) or (230–400 mesh; Merck) as appropriate. Thin layer chromatography analysis is performed on glass mounted silica gel plates (200–300 mesh; J. T. Baker) and visualized using uv light, 5% phosphomolybdic acid in EtOH, or ammonium molybdate/ceric sulfate in 10% aqueous $H_2SO_4$.

Example 1

Preparation of 11-oximyl-13,14-dihydro-16-phenylthio-16tetranor $PGD_1\alpha$ (1j):

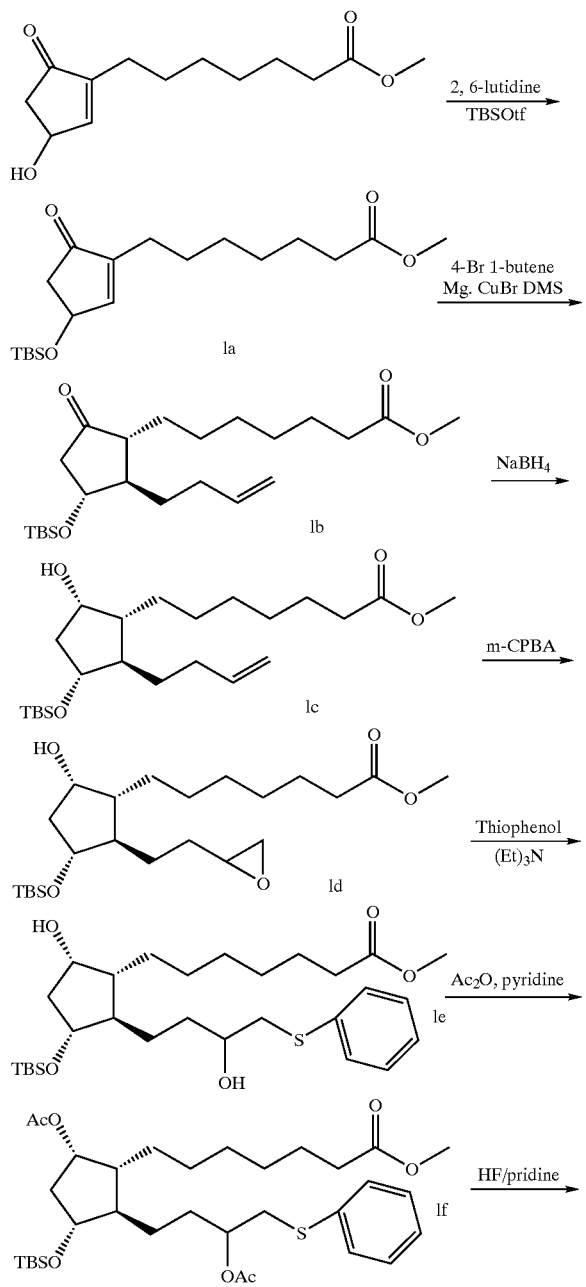

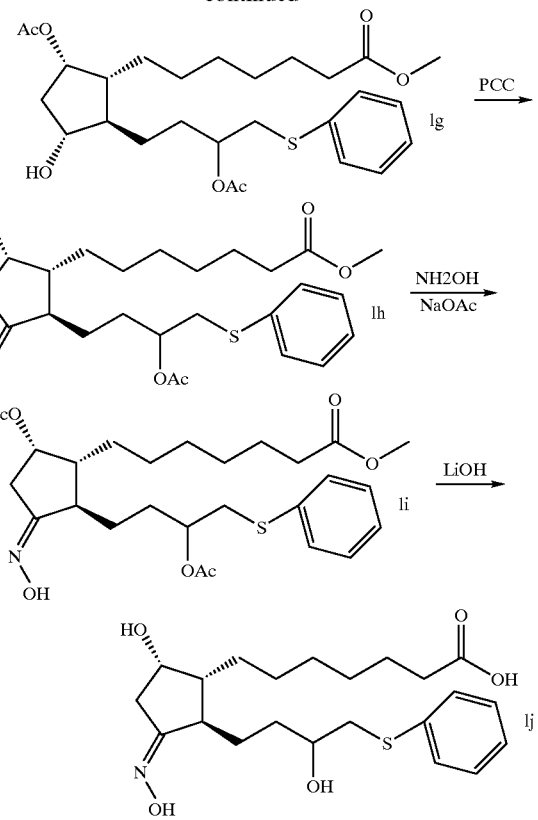

a. Methyl 7-(2-oxo-4-(1,1,2,2-Tetramethyl-1-silapropoxy)cyclopent-1-enyl) Heptanoate (1a): To a solution of Methyl-7-[3-(R)-hydroxy-5-oxo-1-cyclopenten-1-yl] heptanoate (1 equiv.) in $CH_2Cl_2$ at −78° C. is added 2,6 lutidine (1.3 equiv.) dropwise over 15 minutes. The solution is kept at −78° C., and TBDMS Triflate (1.2 equiv.) in $CH_2Cl_2$ is added dropwise over 15 minutes. The reaction is warmed gradually to room temperature and stirred at room temperature for 15 hours. Aqueous 10% HCl is added and the layers are separated. The water layer is extracted with $CH_2Cl_2$ and the organic layers are combined. The organic layer is ished with brine, dried ($Na_2SO_4$) and concentrated. The residue is distilled under vacuum (10 mm Hg) to provide the silyl ether 1a as a yellow liquid.

b. Methyl 7-(5-but-3-enyl-2-Hydroxy-4-(1,1,2,2-tetramethyl-1-silapropoxy) cyclopentyl) Heptanoate (1c): To a slurry of $Mg^0$ powder (2 equiv.) in THF at room temperature is added one crystal of 12 and 1-bromobutene (2 equiv.) dropwise over 10 minutes. The reaction proceeds to exotherm as the addition continues. After the addition is complete, the reaction is refluxed for 3 hours and cooled to room temperature. The Grignard is diluted with THF and added via cannula to a 3-necked flask equipped with mechanical stirring and charged with CuBr.DMS (2 equiv.) in a 1:1 solution of THF/DMS at −78° C. After the addition of the Grignard (~20 min), the reaction is stirred for 1 hour at −78° C. The color of the reaction is dark red at this point. A solution of the ketone 1a (1 equiv.) in THF is then added dropwise over 25 minutes. The reaction is stirred at −78° C. for 15 minutes, then allowed to warm slowly to room temperature over 2 hours. The reaction is quenched with aqueous $NH_4Cl$ and the excess DMS is allowed to evaporate overnight. The reaction is partitioned between brine/$CH_2Cl_2$ and the layers are separated. The aqueous layer is back-extracted with CH$_2$Cl$_2$ and the organic layers are combined and dried (Na$_2$SO$_4$). The solvent is removed in vacuo and the residue is chromatographed on SiO$_2$ (10% hexane/EtOAc) to give the ketone 1b as a clear oil.

The ketone 1b (1 equiv.) is dissolved in MeOH and cooled to −40° C. Sodium borohydride (0.9 equiv.) is added portionwise over 10 minutes. After the addition is complete, the reaction is stirred for 13 hours at −40° C. and then for 12 hours at −78° C. The reaction is quenched with water, partitioned between brine and CH$_2$Cl$_2$, and the layers separated. The aqueous layer is back-extracted with CH$_2$Cl$_2$ and the organic layers are combined and dried (Na$_2$SO$_4$). The solvent is removed in vacuo and the residue chromatographed on SiO$_2$ (30% EtOAc/hexanes) to give the alcohol 1c as a colorless oil.

c. Methyl 7-(2-Hydroxy-5-(2-(2-oxiranyl)ethyl-4-(1,1,2,2-tetramethyl-1-sila-propoxy)cyclopentyl) Heptanoate (1d): The alcohol 1c (1 equiv.) is dissolved in CH$_2$Cl$_2$ and cooled to 0° C. Sodium bicarbonate is added, followed by m-CPBA (57%–85% purity) (3 equiv.) portionwise over 15 minutes. After the addition is complete, the reaction is stirred for 20 hours at room temperature. The reaction is poured into water, partitioned between brine and CH$_2$Cl$_2$, and the layers are separated. The aqueous layer is back-extracted with CH$_2$Cl$_2$ and the organic layers are combined and dried (Na$_2$SO$_4$). The solvent is removed in vacuo and the residue is chromatographed on SiO$_2$ (20% EtOAc/hexanes) to give the epoxide diastereomers Id as a colorless oil.

d. 13,14-Dihydro-16-phenylthio tetranor PGF$_1$α (1e): In a 5 mL round-bottomed flask, epoxide 1d (1 equiv.) and 100 uL of dry benzene are added. The flask is cooled to 0° C., then is treated with 60 uL of thiophenol (1.2 eq ) and 78 uL of triethyl amine (1.2 eq ) as disclosed in J. G. Smith, "Synthetically Useful Reactants of Epoxides", *Synthesis* (1984) p. 629–656, and references cited therein. The ice bath is removed and the reaction is stirred at room temperature under nitrogen overnight. TLC is used to monitor the reaction. Excess thiophenol is added if necessary. The reaction is quenched with brine and is extracted with methylene chloride. The organic layer is ished three times with IN HCl, brine, dried over sodium sulfate, and concentrated to yield 1e.

e. Methyl 9,15-Acetyl 13,14-dihydro-16-phenylthio tetranor PGF$_1$α (1g): In a 25 mL round-bottom flask, diol 1e (1 equiv.) and of acetic anhydride (2 mL ) is stirred in pyridine (10 mL) overnight. The reaction is concentrated under reduced pressure. The residue is dissolved in dichloromethane (40 mL) and washed 2 times with 1 N HCl. The organic layer is dried with MgSO$_4$ and solvent removed in vacuo leaving crude (1f).

The crude 1f is treated with HF/pyridine (6 equiv.) in dry acetonitrile (10 mL). The mixture is stirred at 0° C. for 2 hours and concentrated under reduced pressure. The crude material is flashed on a silica gel column using 30% ethyl acetate in hexane. Appropriate fractions were pooled and concentrated giving (1g) as a colorless oil.

f. Methyl 9,15-Acetyl 13,14-dihydro-16-phenylthio tetranor PGD$_1$α (1h): In a 50 mL round-bottom flask, alcohol 1g (1 equiv.) is added to dichloromethane (20 mL) with 10 grams of powdered molecular sieves. PCC (3 equiv.) is then added, and the solution is stirred overnight. The mixture is filtered through Floracil and concentrated to a yellow oil (1h).

g. Methyl 9,15-acetyl 11-Oximyl-13,14-dihydro-16-phenylthio tetranor PGD$_1$α (1i): In a 25 mL round bottom flask is added ketone 1h (1 equiv.), sodium acetate (9 equiv.), and hydroxyl amine (2 equiv.); in 3:1:1 (MeOH: dioxane: water) (5 mL). The solution is stirred overnight, and ether (50 mL) is added. The organic layer is then washed with 1N HCl and brine. The organic layer is then dried with MgSO$_4$ and concentrated under reduced pressure. The crude material is flashed on silica gel using 30% ethyl acetate in hexane. Appropriate fractions were collected and concentrated to a yellow liquid (1i).

h. 11-Oximyl-13,14-dihydro-16-phenylthio-16-tetranor PGD$_1$α (1j): In a 15 mL round-bottom flask is added 1i (1 equiv.), and LiOH (3 equiv.) in 3:1 (THF:water). The mixture is stirred overnight and concentrated under reduced pressure. The residue is flashed on a silica gel column in 5% MeOH:dichloromethane with 0.1% acetic acid. Appropriate fractions were combined, and concentrated to give a colorless oil (1j).

Examples 2–15

Examples 2–15 are prepared using substantially the same procedures as those described in Example 1, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 2

11-Oximyl-13,14-dihydro-16-(2,4-difluorophenylthio)-16-tetranor-PGD$_1$ Methyl Ester

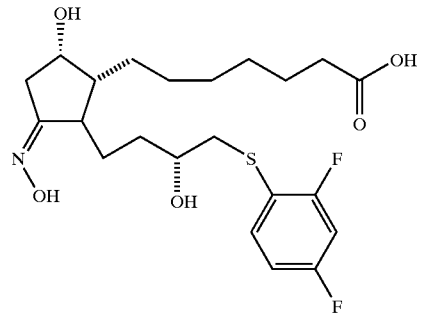

Example 3

11-Oximyl-13,14-dihydro-16-(2,4-difluorophenoxy)-16-tetranor PGD$_1$

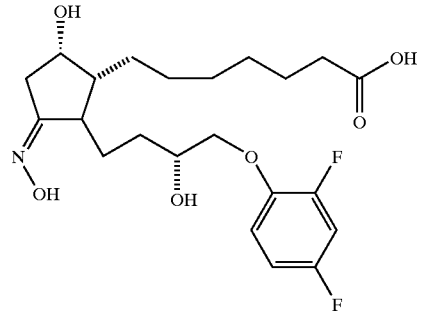

Example 4

11-Oximyl-13,14-dihydro-16-aza-17-(2,4-fluorophenyl)-17-trinor-PGD$_1$ Methyl Ester

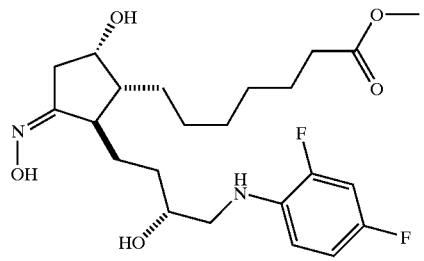

Example 5

11-Oximyl-13,14-dihydro-16-(4-fluorophenylthio)-16-tetranor PGD$_1$ Ethyl Ester

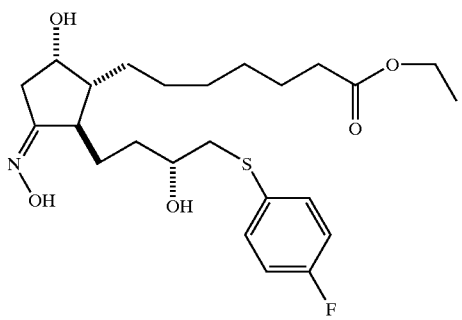

Example 6

11-Oximyl-13,14-dihydro-16-(4-fluorophenoxy)-16-tetranor PGD$_1$

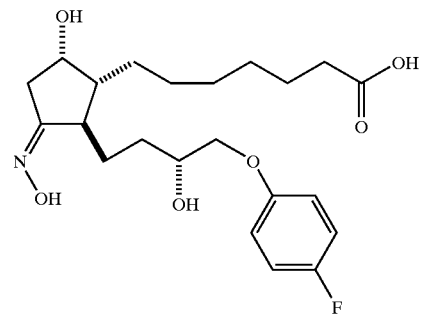

Example 7

11-Oximyl-13,14-dihydro-16-(3-chlorophenoxy)-16-tetranor PGD$_1$

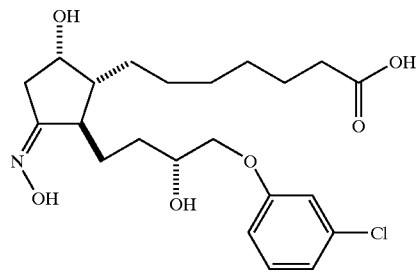

Example 8

11-Oximyl-13,14-dihydro-16-methyl-16-(3-chlorophenoxy)-16tetranor PGD$_1$

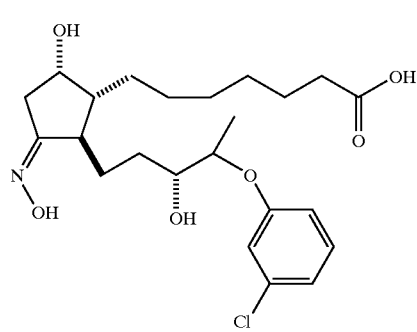

Example 9

11-Oximyl-13,14-dihydro-16-(2-methoxyphenylthio)-16-tetranor PGD$_1$

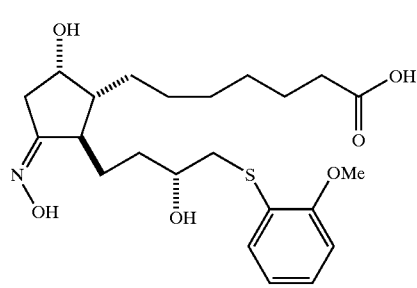

Example 10

11-Oximyl-13,14-dihydro-16-(3-methoxyphenylthio)-16-tetranor $PGD_1$ Isopropyl Ester

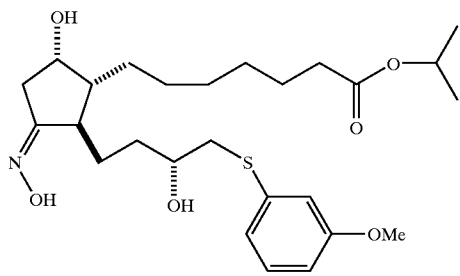

Example 11

11-Oximyl-13,14-dihydro-16-(thiomethyl-(2-thienyl))-16-tetranor $PGD_1$ Methyl Ester

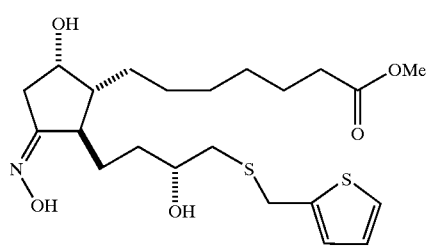

Example 12

11-Oximyl-13,14-dihydro-16-((3-trifluoromethyl)phenoxy)-16-tetranor $PGD_1$ Methyl Ester

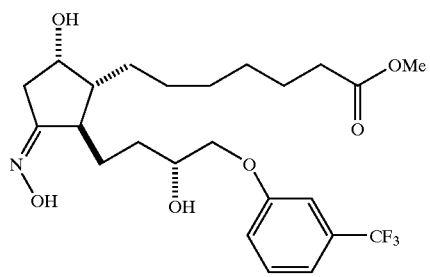

Example 13

11-Oximyl-13,14-dihydro-16-(2-methylphenoxy)-16-tetranor $PGD_1$ Glyceryl Ester

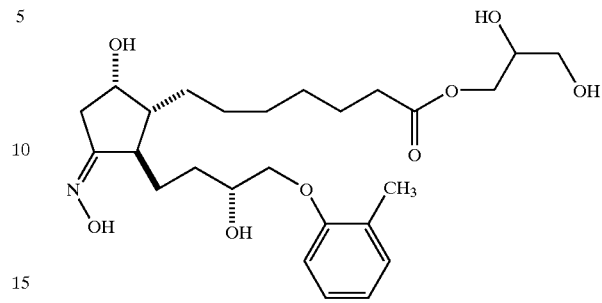

Example 14

11-Oximyl-13,14-dihydro-16-(3-methylphenylthio)-16-tetranor $PGD_1$

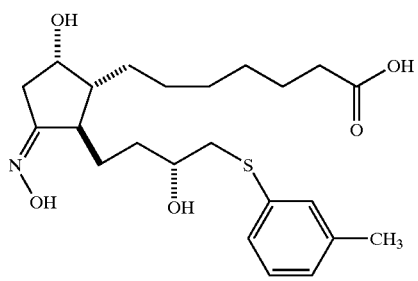

Example 15

11-Oximyl-13,14-dihydro-16-phenylthio-16-tetranor $PGD_1$ Methyl Ester

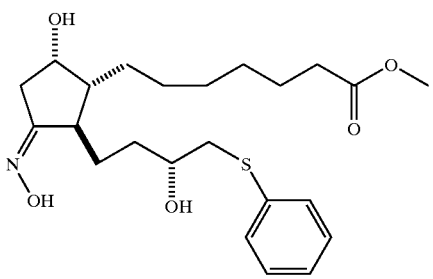

Example 16

Preparation of 11-Oximyl-16-(2-fluorophenoxy)-16-tetranor-$PGD_2\alpha$ (1n):

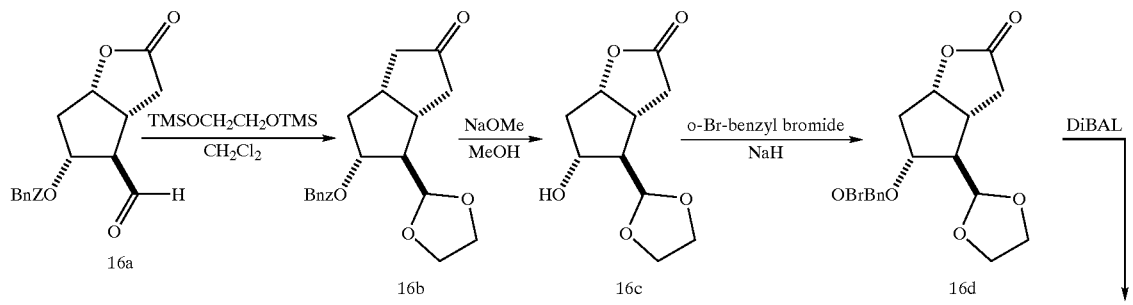

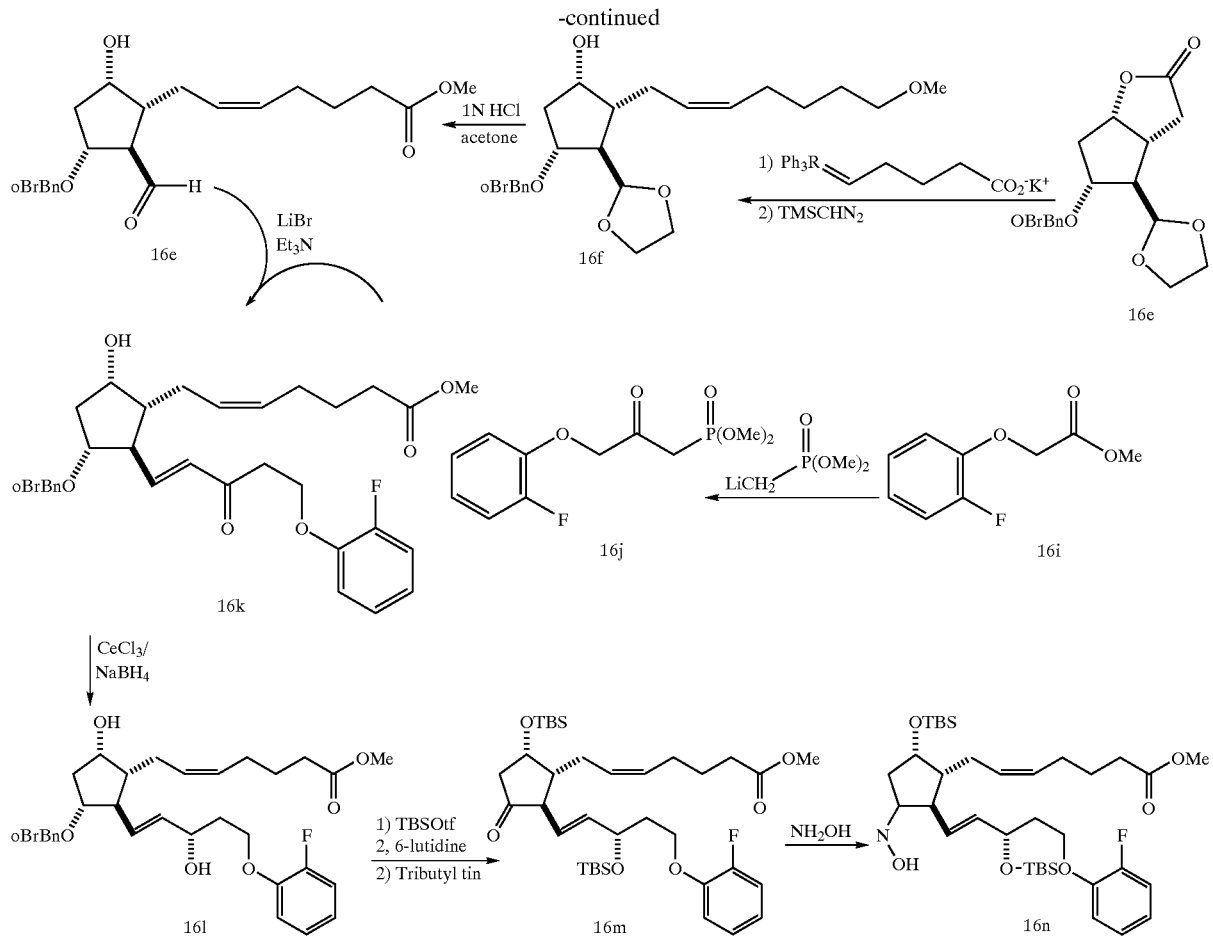

a. 7-Benzoyfoxy-6-(2,5-dioxolanyl)-2-oxabicyclo[3.3.0] octan-3-one (16b): In a round bottom flask equipped with a magnetic stir bar is placed 1,2-bis(trimethylsilyloxy) ethane in methylene chloride at −78° C. To this is added, within 20 minutes, a solution of 16a in CH$_2$Cl$_2$. The reaction is stirred for 1 hour at −78° C. and then slowly warmed to 25° C. for 1 hour. The reaction is quenched at 0° C. with water, extracted with methylene chloride, is dried over MgSO$_4$, and is concentrated in vacuo to give crude 16b (FW=318.32 g/mole).

b. 6-(2,5-Dioxolanyl)-7-hydroxy-2-oxabicyclo[3.3.0] octan-3-one (16c): To a well stirred solution of crude 16b (63.85 g, 201 mmol, 1 eq) in methanol (786 m.L) at 0° C. is added a suspension of sodium methoxide (13.27 g, 246 mmol, 1.2 eq) in MeOH (98.3 mL). The reaction is stirred at 0° C. for 1 hour and then is warmed to 25° C. for 1 h. The reaction is neutralized with acidic ion exchange resin which has been washed thoroughly with MeOH (5×100 mL). The filtrate is concentrated in vacuo to give a syrup which is subjected to flash chromatography on silica gel eluting with 4:1 hexane : ethyl acetate and 2% MeOH in CH$_2$Cl$_2$ to give 16c as a yellow syrup.

c. 6-(2,5-Dioxolanyl)-2-oxa-7-(o-bromobenzyloxy) bicyclo [3.3.0] octan-3-one (16d): In a round bottom flask with a magnetic stir bar, is stirred a solution of 16c in CH$_2$Cl$_2$. To this solution is added dropwise at −78° C. a suspension of NaH. The reaction is stirred for 30 minutes at −78° C. and then ortho-bromo benzyl bromide is added and the reaction is warmed to 25° C. overnight. The reaction is quenched with water (100 mL). The organic layer is washed with water (3×100 mL), dried over MgSO$_4$, and concentrated in vacuo to give a yellow oil which is subjected to flash chromatography on silica gel eluting with hexanes then 1% MeOH in CH$_2$Cl$_2$. The product is then washed with 1N HCl, 0.1N HCl, water and brine to give 16d.

d. Methyl 7-(5-(2,5-Dioxolanyl)-2-hydroxy-4-(o-bromobenzyloxy) Cyclopentyl) hept-5-enoate (16f): In a round bottom flask with a magnetic stir bar, is stirred a solution of 16d in dry toluene. To this solution, at −78° C., is slowly added DIBAL in hexane. The reaction mixture is stirred for 2 hours and then warned to 0° C. Saturated is added to the reaction mixture which is then slowly warmed to 25° C. Diluted with water (100 mL), the insoluble precipitate is removed by suction filtration and the solid is washed with EtOAc (2×25 mL). The liquid phase is extracted with EtOAc (3×50 mL) and the combined organic phase is dried over MgSO$_4$ and is concentrated in vacuo to give a yellow syrup. The product, 16c, must either be used immediately or stored at −70° C. overnight. To a suspension of (4-carboxybutyl)triphenylphosphonium in THF at 0° C. under Nitrogen is added dropwise a solution of KHMDS in toluene. The resulting deep orange colored reaction mixture is stirred for 1 hour at 25° C. To the reaction mixture above at −78° C. is added a solution of 16e in THF. The reaction mixture is allowed to warm to 25° C. overnight. The reaction is quenched with water at 0° C. and the pH is adjusted to 3.5–4.0 with 1N HCl. The water phase is extracted with EtOAc and the combined organic phase is dried over MgSO$_4$ and is concentrated in vacuo to give a syrup containing crude acid. To a well stirred solution of acid in and MeOH at 0° C.

is added TMS diazomethane until the reaction mixture keeps a light yellow color. The addition of 1 drop of acetic acid, glacial and thin layer chromatography verifies the reaction has gone to completion. The reaction solution is concentrated in vacuo and is purified via flash chromatography on silica gel eluting with 30% EtOAc in hexanes yielding 16f.

e. Methyl 7-(2-Hydroxy-4-(o-bromobenzyloxy)-5-formyl-cyclopentyl) hept-5-enoate (16g): In a round-bottomed flask with a magnetic stir bar is placed an amount of the ketal, 16f. To this flask is added a sufficient amount of a mixture of 2 parts acetone to 1 part 1N HCl to bring the ketal completely into solution. This material is stirred until, by TLC, the starting material is consumed, typically overnight. The crude mixture, containing the product 16g, is extracted with ether, and the ether extract re-esterified in situ with, preferably, TMS-diazomethane. The organic extracts were concentrated under reduced pressure at 0° C. and used immediately without further purification.

f. Dimethyl-3-(2-Fluorophenoxy)-2-oxo-butylphosphonate (16j): In a flame-dried, round-bottomed flask equipped with a stir bar and thermometer is placed dimethylmethyl phosphonate (1.0 equiv.) in anhydrous THF. The solution is cooled to −78° C. and treated with n-butyllithium (1.05 equiv.). The reaction mixture is allowed to stir for 15 minutes. To this solution is added methyl-2-(2-fluorophenoxy)propionate (1.1 equiv.) in anhydrous THF. The mixture is allowed to warm to room temperature over the next 6 hours. The mixture is treated with a saturated solution of ammonium chloride and extracted with $CH_2Cl_2$. The organic layer is washed with water followed by brine. The combined aqueous layers are back extracted with $CH_2Cl_2$ and the organic layers combined, dried over anhydrous $MgSO_4$, filtered, and concentrated under reduced pressure. Purification is effected by silica gel column chromatography (hexane/ethyl acetate/2-propanol 45/50/5 to hexane/ethyl acetate/2-propanol 40/50/10) to yield 1.34 g (70%) of dimethyl-4-(2-fluorophenyl)-2-oxo-butylphosphonate (16j) as an oil.

g. 11-o-Bromobenzyloxy-16-(2-Fluorophenoxy)-17-trinor-15-oxo-$PGF_2\alpha$ Methyl Ester (16k): In a flame-dried, round-bottomed flask equipped with a magnetic stirbar is placed dimethyl-4-(2-fluorophenyl)-2-oxo-butylphosphonate (16j) (1.43 equiv) in DME and water. To this solution is added lithium bromide (1.65 equiv), triethylamine (1.65 equiv), and (16g) (1.0 equiv). The solution is stirred at room temperature for 48 hours. At this point additional triethylamine and water is added and the solution is stirred for an additional hour. The solution is poured into brine and extracted with 3 portions of ethyl acetate. The organic layers are combined, dried over anhydrous $MgSO_4$, filtered, and concentrated under reduced pressure. Purification is effected by silica gel column chromatography (dichloromethane/methanol 19/1) to give 11-o-bromobenzyloxy-17-(2-fluorophenyl)-17-trinor-15-oxo-$PGF_{2a}$ methyl ester (1k) as an oil.

h. 11-o-Bromobenzyloxy-15-(R,S)-16-(2-fluorophenoxy)-17-trinor-$PGF_{2a}$ Methyl Ester (16l): In a flame-dried round-bottomed flask equipped with a stir bar is placed 17-(2-fluorophenyl)-17-trinor-15-oxo-$PGF_{2a}$ methyl ester (16k) (1.0 equiv), cerium trichloride (1.05 equiv) in methanol. The solution is stirred at room temperature for 5 minutes. The solution is cooled to −10° C. and sodium borohydride (1.02 equiv.) in methanol is added. The solution is stirred at −10° C. for 3 hours. The mixture is treated with water and the pH brought to 6–7 with 1N hydrochloric acid. The mixture is extracted twice with ethyl acetate, and the organic layers combined, dried over anhydrous $MgSO_4$, filtered and concentrated under reduced pressure. Purification is effected by silica gel column chromatography (3% methanol in dichloromethane to 5% methanol in dichloromethane) to give the 15 (R) epimer and the 15 (S) epimer as colorless oils.

i. 9,15-bis-tert-Butyldimethylsilyloxy-13,14-dihydro-16-(2-fluorophenoxy)-17-trinor-$PGD_2$ Methyl Ester (16m): In a round-bottomed flask equipped with a magnetic stirbar, is stirred a solution of 16l (1 equiv) in $CH_2Cl_2$. To this solution is added dropwise at −78° C. 2,6-lutidine (2.9 equiv.) followed by TBDMSOTf (2.8 equiv.). The reaction stirred for 30 minutes at −78° C. and then warmed to 25° C. overnight. The reaction is quenched with water. The organic layer is washed with water, dried over $MgSO_4$, and concentrated in vacuo to give a yellow oil which is subjected to flash chromatography on silica gel eluting with hexanes then 1% MeOH in $CH_2Cl_2$. The product is then washed with 1N HCl, 0.1N HCl, water, and brine to give the bis-protected intermediate. This intermediate is placed in a flame-dried round-bottomed flask equipped with a stir bar. Tri-n-butyl tin hydride is added to Ether and the reaction is stirred for 24 hours. Quenching with 1N HCL and then back washing the organics 2 with with brine. Dry over $MgSO_4$ and the organic layer is concentrated under reduced pressure and chromatographed to yield the PGD analog 16m.

j. 11-Oximyl-13,14-dihydro-16-(2-fluorophenoxy)-17-trinor-$PGD_2$ (16n): A round-bottomed flask equipped with a stirbar is cooled to 0° C. and the methyl ester (16m) and a solution of HF in pyridine are added. The solution is allowed to warm to room temperature and followed by TLC. Upon consumption of the starting material, the solution is concentrated and partitioned between ethyl acetate and 0.1% aqueous sodium carbonate. The organic extracts are combined and chromatographed and the crude product is stirred overnight with hydroxylamine and sodium acetate (1:9) in 1:1:3 p-dioxane: water: methanol. The mixture is concentrated under reduced pressure and added is lithium hydroxide monohydrate (1.8 equiv) in a 50/50 THF/water solution. The mixture is stirred at room temperature for 6 hours and then diluted with water and acidified to pH 2–3 with 1N HCl. The aqueous phase is extracted 3 times with ethyl acetate and the organic layers combined. The combined organic layers were dried over anhydrous $MgSO_4$, filtered, and concentrated under reduced pressure to yield the crude acid. Purification is effected by HPLC to yield an analytical sample of 16n.

Examples 17–28

Examples 17–28 are prepared using substantially the same procedures as those described in Example 16, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 17

11-Oximyl-16-(2,4-difluorophenylthio)-17-trinor-$PGD_2$ Methyl Ester

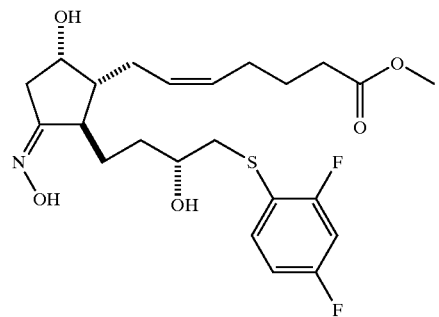

Example 18

11-Oximyl-16-aza-(3,5-difluorophenyl)-17-trinor PGD$_2$

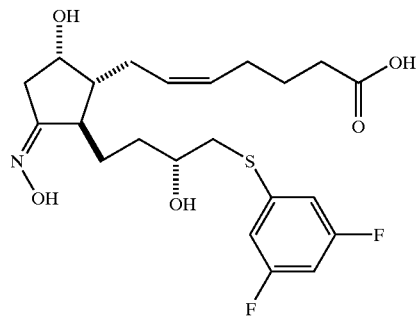

Example 19

11-Oximyl-16-(2-fluorophenylthio)-17-trinor-PGD$_2$ Methyl Ester

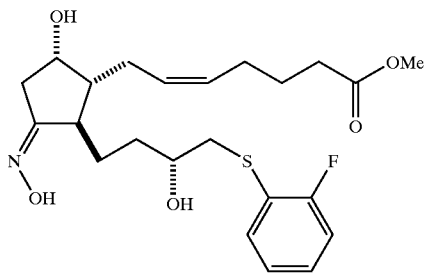

Example 20

11-Oximyl-16-(4-fluorophenoxy)-16-tetranor PGD$_2$ Ethyl Ester

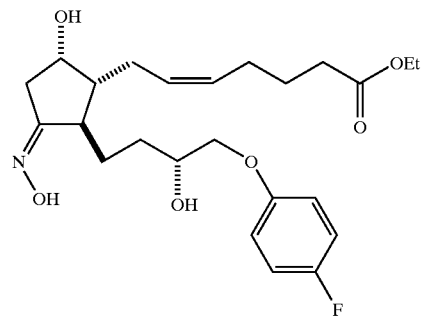

Example 21

11-Oximyl-16-(4-fluorophenylthio)-16-tetranor PGD$_2$

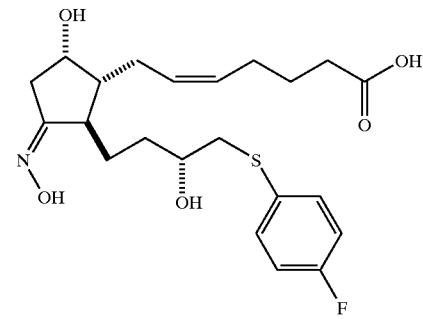

Example 22

11-Oximyl-16-(2-methoxyphenoxy)-16-tetranor PGD$_2$

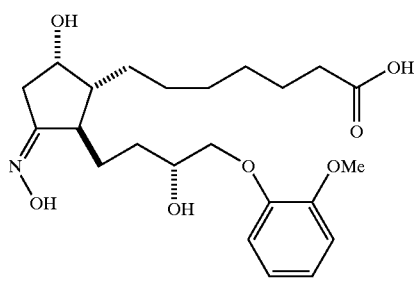

Example 23

11-Oximyl-16-(3-methoxyphenoxy)-16-tetranor PGD$_2$ Iso-propyl Ester

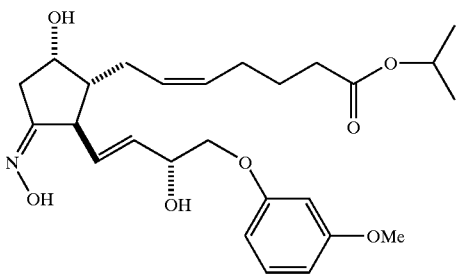

Example 24

11-Oximyl-17-oxo-(2-methyl-thienyl)-18-dinor PGD$_2$ Methyl Ester

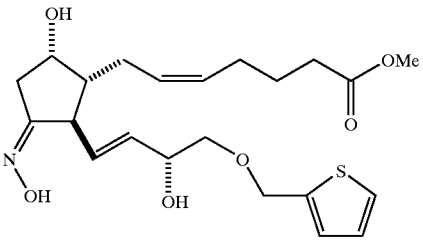

Example 25
11-Oximyl-16-((3-trifluoromethyl)phenoxy)-16-tetranor PGD$_2$ Methyl Ester
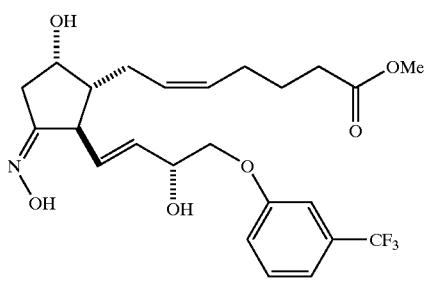
Example 26
11-Oximyl-16-(2-methylphenoxy)-16-tetranor PGD$_2$ Methyl Ester
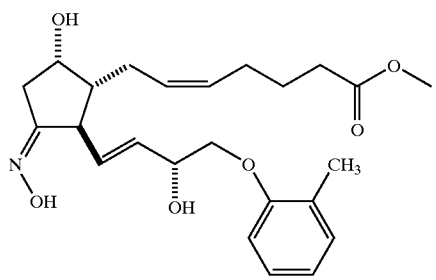
Example 27
11-Oximyl-16-(3-methylphenoxy)-16-tetranor PGD$_2$
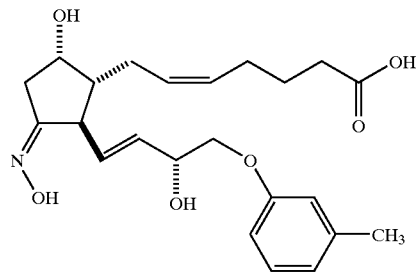
Example 28
11-Oximyl-16-phenoxy-16-tetranor PGD$_2$
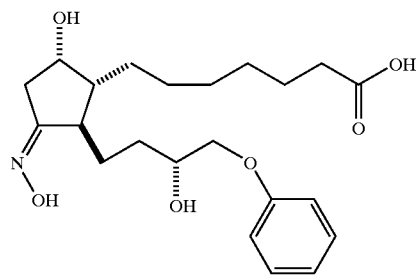
Example 29
Preparation of 11-Oximyl-13,14-dihydro-16-phenylthio 16-tetranor PGD$_1\alpha$ (29b):
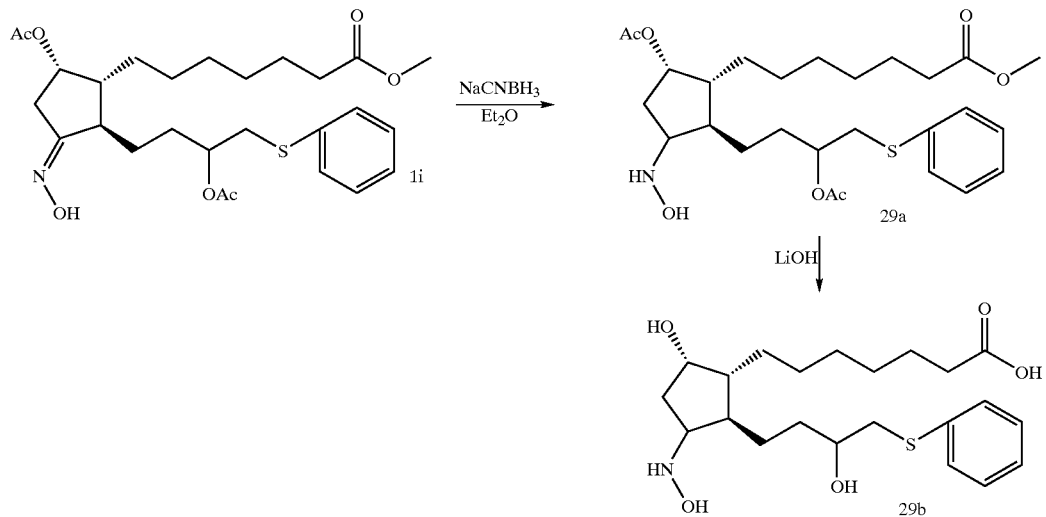

Compound 1i from Example 1 is treated with sodium cyanoborohydride in THF: acetic acid (1:1) and allowed to react for 2 hours. The mixture is quenched with 1 N HCl and washed with brine twice. The organic layer is dried over magnesium sulfate and reduce under pressure. The resulting oil is chromatographed using 30% ethyl acetate: hexane. Appropriate fractions were combined and reduced to a yellow oil, yielding 29a. Deprotection is accomplished by methods described above, yielding 29b.

Examples 30–34

Examples 30–34 are prepared using substantially the same procedures as those described in Example 29, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 30

11-Hydroxylamino-13,14-dihydro-16-(3-chlorophenoxy)-16-tetranor -PGD$_1$

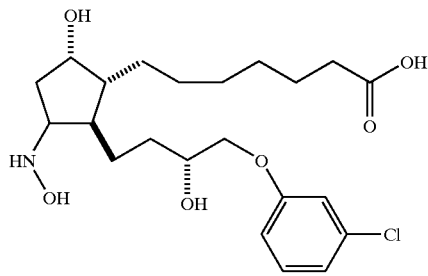

Example 31

11-Hydroxylamino-13,14-dihydro-16-(2,4-difluorophenylthio)-16-tetranor PGD$_1$ Methyl Ester

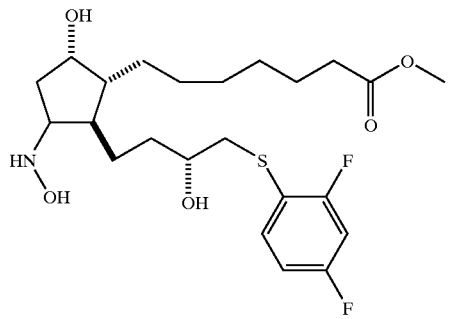

Example 32

11-Hydroxylamino-13,14-dihydro-16-aminophenyl-16-tetranor -PGD$_1$

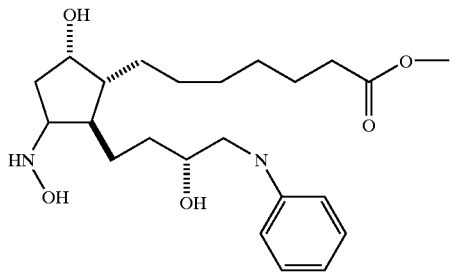

Example 33

11-Hydroxylamino-13,14-dihydro-16-(4-fluorophenylthio)-16-tetranor PGD$_1$ Ethyl Ester

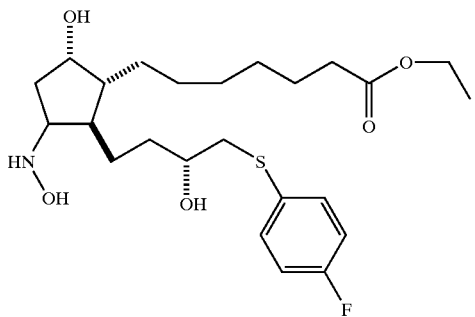

Example 34

11-Hydroxylamino-13,14-dihydro-16-(4-fluorophenoxy)-16-tetranor PGD$_1$

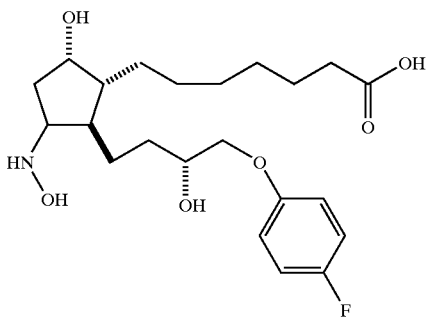

Example 35

11-Hydroxylamino-16-phenoxy-16-tetranor-1-tetrazolyl PGD$_2$

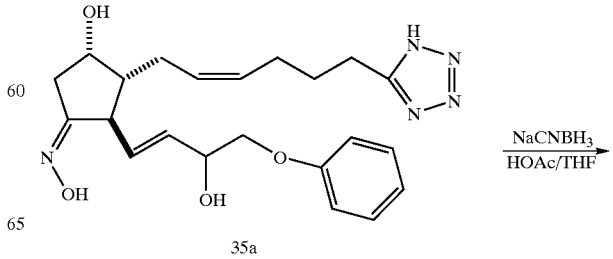

35a

-continued

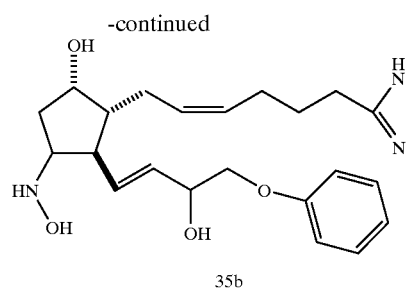

35b 11-oximyl-16-phenoxy-16-tetranor-1-tetrazolyl $PGD_2$ is prepared using substantially the same procedures as those described in Example 16, substituting the tetrazoyl phosphonium salt for the carboxylate and phenyl for the o-fluorophenyl. To this compound (35a) is added 1.5 equiv. of sodium cyanoborohydride in a 1:1 mixture of acetic acid and tetrahydrofuran. The reaction is monitored by TLC. After complete consumption of starting material, the reaction is diluted with water and exhaustively extracted with EtOAc, yielding the hydroxylamine.

Examples 36–40

Examples 36–40 are prepared using substantially the same procedures as those described in Example 35, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 36
11-Hydroxylamino-16-phenylthio-16-tetranor -$PGD_{2a}$

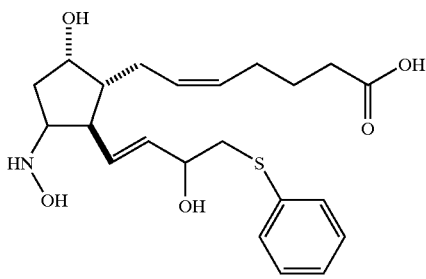

Example 37
11-Hydroxylamino-20-ethoxy- $PGD_{2a}$

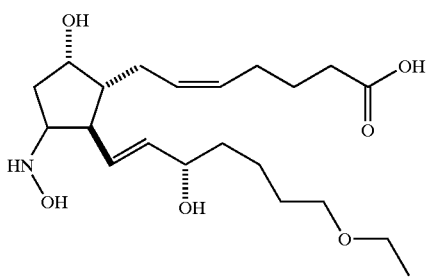

Example 38

11-Methoxylamino-16-(3,5-difluorophenoxy)-16-tetranor $PGD_{2a}$

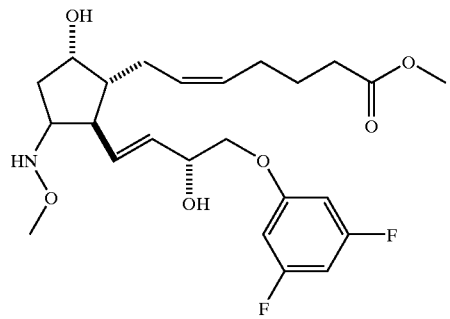

Example 39

11-Hydroxylamino-16-(3-thiofuranyl)-17-trinor-$PGD_{2a}$

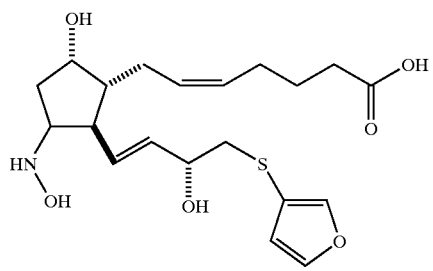

Example 40

11-Hydroxylamino-16-((3-trifluoromethyl)phenoxy)-17-trinor $PGD_{2a}$

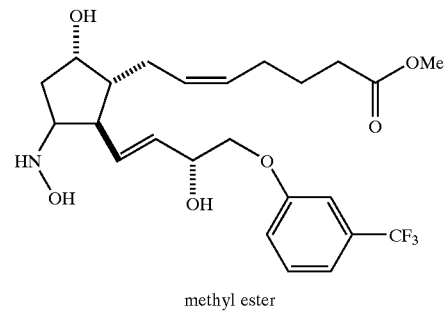

methyl ester

Example 41
11-Oximyl-15-methyl-16-2-fluorophenoxy-17-trinor-PGD$_2$Methyl Ester

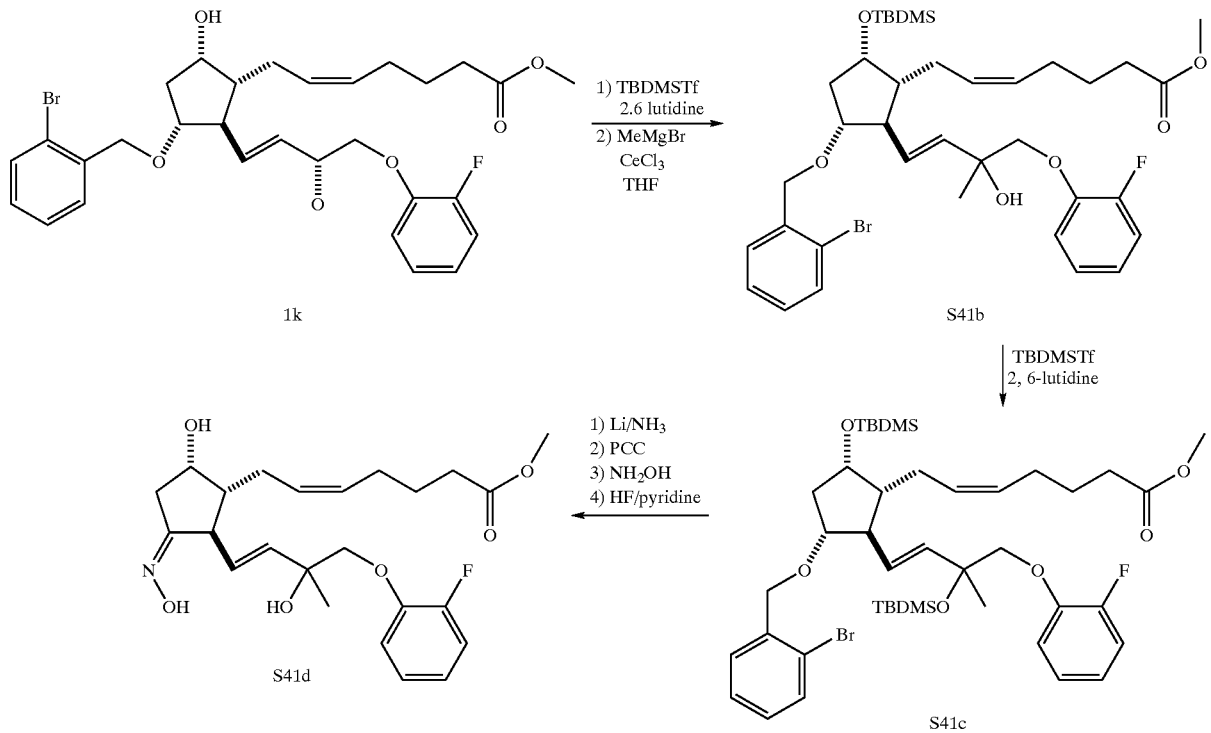

Compound 16k from Example 16 is dissolved in dry THF and 1.2 equiv. of TBDMSOTf and 1.5 equiv. of 2,6 lutidine are added. Standard work-up yields the TBDMS-protected version of 16k, which is dissolved in THF. Addition of the methylcerium nucleophile (1.5 equiv.) (for examples of cerium chloride-mediated nucleophilic addition see: T. Imamoto, et al., "Carbon-Carbon Bond Forming Reactions Using Cerium Metal or Organocerium (III) Reagents", *J. Org. Chem.* Vol. 49 (1984) p. 3904–12; T. Imamoto, et al., "Reactions of Carbonyl Compounds with Grignard Reagents in the Presence of Cerium Chloride", *J. Am. Chem. Soc.* Vol. 111 (1989) p. 4392–98; and references cited therein) gives the product S41c, which after purification is dissolved in liquid ammonia and a sufficient amount of lithium metal is added to effect deprotection of the benzyl ether. After purification, the deprotected S41c is condensed with hydroxylamine as described in Example 1 and deprotected to yield the title compound, S41d.

Examples 42–43

Examples 42–43 are prepared using substantially the same procedures as those described in Example 41, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 42
11-Oximyl-15-ethyl-17-phenoxy-18-dinor-PGD$_2$

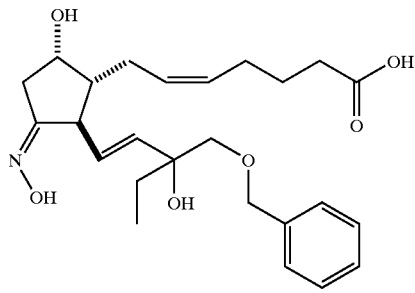

Example 43
3-oxo-11-Oximyl-13,14-dihydro-15-methyl-16-phenoxy-16-tetranor -PGD$_{1\alpha}$

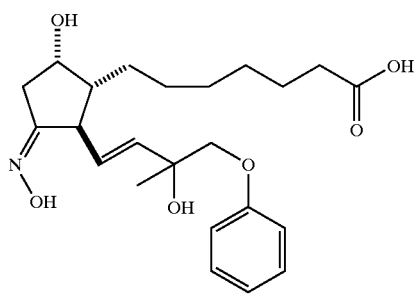

Example 44

3-oxo-11-Hydroxylamino-13,14-dihydro-15-methyl-16-phenoxy-16-tetranor-PGD$_{1\alpha}$

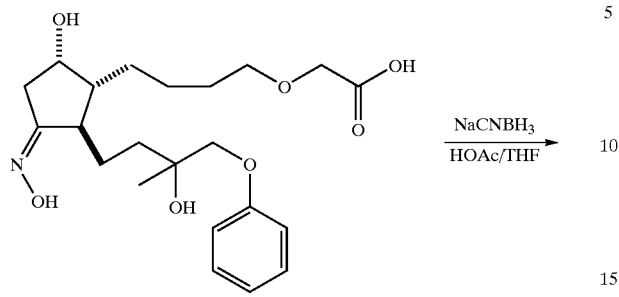

To a 50 mL round bottom flask is 3-oxo-11-oximyl-13,14-dihydro-15-methyl-16-phenoxy-17-trinor-PGD$_2$ (from Example 43) and 1.5 equiv. of sodium cyanoborohydride in a 1:1 mixture of acetic acid and tetrahydrofuran. The reaction is monitored by TLC. After complete consumption of starting material, the reaction is diluted with water, the pH is adjusted to 3.0, and exhaustively extracted with EtOAc, yielding the title hydroxylamine-containing PGF analog.

Example 45

11-oximyl-15-methyl-15-deoxy-15-methamino-16-2-fluorophenoxy-16-tetranor-PGD$_2$ Methyl Ester

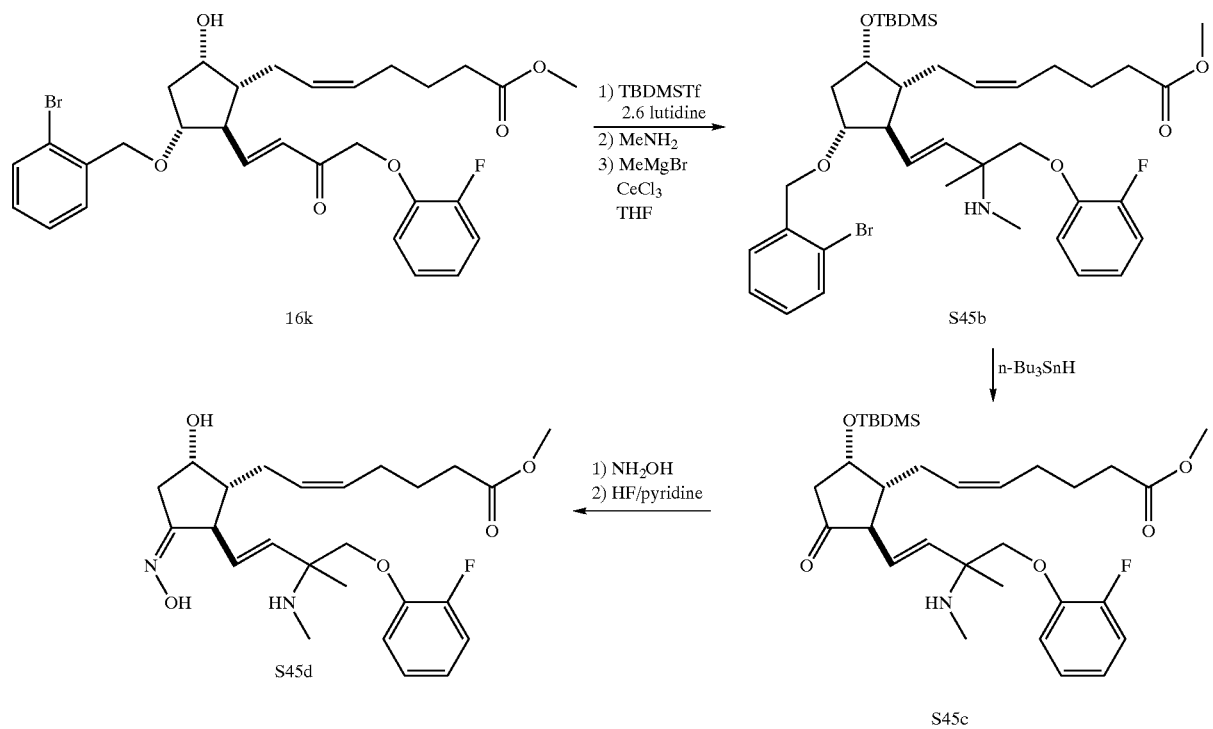

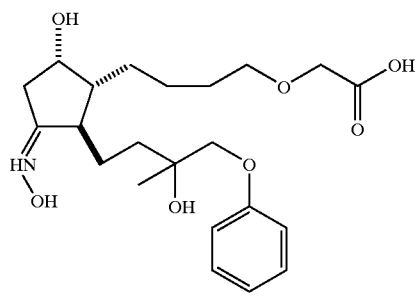

Compound 16k from Example 16 is dissolved in dry THF and 1.2 equiv. of TBDMSTf and 1.5 equiv. of 2,6 lutidine are added. Standard work-up yields the TBDMS-protected version of 16k, which is dissolved in THF and condensed with methylamine to give the intermediate imine. Addition of the methylcerium nucleophile (~1.5 equiv.) (for examples of cerium chloride-mediated nucleophilic addition see: T. Imamoto, et al., "Carbon-Carbon Bond Forming Reactions Using Cerium Metal or Organocerium (III) Reagents", *J. Org. Chem.* Vol. 49 (1984) p. 3904–12; T. Imamoto, et al., "Reactions of Carbonyl Compounds with Grignard Reagents in the Presence of Cerium Chloride", *J. Am. Chem. Soc.* Vol. 111 (1989) p. 4392–98; and references cited therein) gives the product S45b, which after purification is dissolved in THF and a sufficient amount of tri-nbutyl tin hydride is added to effect the oxidative removal of the benzyl ether. After purification, S45c is condensed with hydroxylamine as described in Example 16 and deprotected to yield the title compound, S45d.

Example 46
11-Hydroxylamino-15-methyl-15-deoxy-15-methylamino-16–2-fluorophenoxy-16-tetranor-PGF$_{2a}$ Methyl Ester

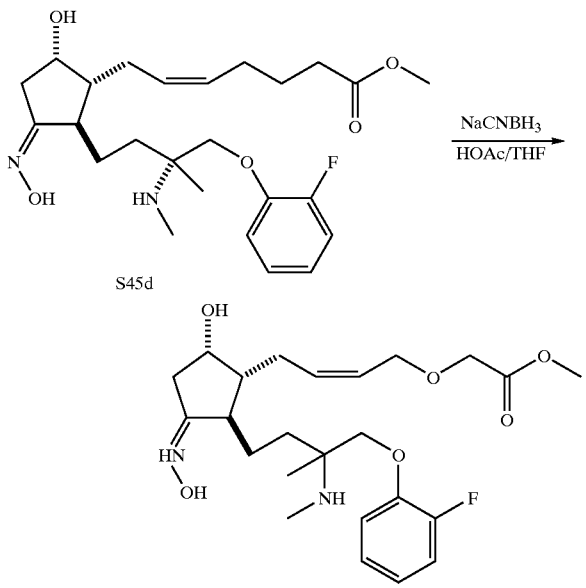

To a 50 mL round bottom flask is charged 11-oximyl-15-methyl-15-deoxy-15-methamino-16-o-fluorophenoxy-17-trinor-PGD$_2$ methyl ester (Example 45) and 1.5 equiv. of sodium cyanoborohydride in a 1:1 mixture of acetic acid and tetrahydrofuran. The reaction is monitored by TLC. After complete consumption of starting material, the reaction is diluted with water and exhaustively extracted with EtOAc, yielding the title hydroxylamine-containing PGF analog.

Example 47
Preparation of 11-Oximyl-13,14-dihydro-16-((3-trifluoromethyl)phenoxy)-16-tetranor-PGD$_1$1-hydroxamic Acid:

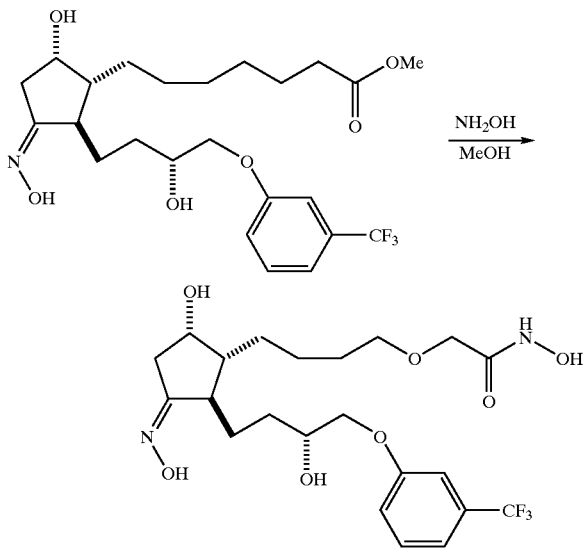

In a flame-dried 25 mL round-bottomed flask equipped with a magnetic stirbar is placed 11-oximyl-13,14-dihydro-16-((3-trifluoromethyl) phenoxy)-17-trinor-PGD$_1$ methyl ester (Example 12) (1.0 equiv.) in methanol. To this solution is added hydroxylamine in methanol (1.25 equiv.). The solution is stirred for 18 hours. The solution is then treated with 1N hydrochloric acid and thrice extracted with ethyl acetate. The organic layer is washed with saturated aqueous sodium chloride, dried over anhydrous MgSO$_4$, filtered and concentrated under reduced pressure. The residue is purified by chromatography to give 11-oximyl-13,14-dihydro-16-((3-trifluoromethyl) phenoxy)-16-tetranor-PGD$_1$ 1-hydroxamic acid.

Example 48
Example 48 is prepared using substantially the same procedures as those described in Example 47, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 48
11-Oximyl-16-phenoxy-17-trinor-PGD$_2$ 1-N-methanesulfonamide

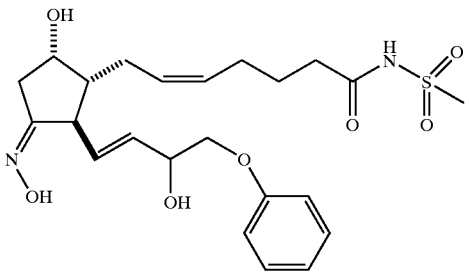

Compositions

Compositions of the subject invention comprise a safe and effective amount of the subject compounds, and a pharmaceutically-acceptable carrier. As used herein, "safe and effective amount" means an amount of a compound sufficient to significantly induce a positive modification in the condition to be treated, but low enough to avoid serious side effects (at a reasonable benefit/risk ratio), within the scope of sound medical judgment. A safe and effective amount of a compound will vary with the particular condition being treated, the age and physical condition of the patient being treated, the severity of the condition, the duration of the treatment, the nature of concurrent therapy, the particular pharmaceutically-acceptable carrier utilized, and like factors within the knowledge and expertise of the attending physician.

In addition to the compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a subject. The term "compatible", as used herein, means that the components of the composition are capable of being commingled with the compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the subject being treated.

Some examples of substances which can serve as pharmaceutically-acceptable carriers or components thereof are sugars, such as lactose, glucose and sucrose; starches, such as cornstarch and potato starch; cellulose and its derivatives, such as sodium carboxymethyl cellulose, ethyl cellulose, cellulose acetate; powdered tragacanth; malt; gelatin; talc; solid lubricants, such as stearic acid, magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; alginic acid; emulsifiers, such as the Tweens®; wetting agents such as sodium lauryl sulfate; coloring agents; flavoring agents, excipients; tableting agents; stabilizers; antioxidants; preservatives; pyrogen-free water; isotonic saline; and phosphate buffer solutions.

The choice of a pharmaceutically-acceptable carrier to be used in conjunction with a compound is basically determined by the way the compound is to be administered. The compounds of the present invention may be administered systemically. Routes of administration include transdermal; oral; parenterally, including subcutaneous or intravenous injection; topical; and/or intranasal.

The appropriate amount of the compound to be used may be determined by routine experimentation with animal models. Such models include, but are not limited to the intact and ovariectomized rat models, the ferret, canine, and non human primate models as well as disuse models.

Preferred unit dosage forms for injection include sterile solutions of water, physiological saline, or mixtures thereof. The pH of said solutions should be adjusted to about 7.4. Suitable carriers for injection or surgical implants include hydrogels, controlled- or sustained release devises, polylactic acid, and collagen matrices.

Suitable pharmaceutically-acceptable carriers for topical application include those suited for use in lotions, creams, gels and the like. If the compound is to be administered perorally, the preferred unit dosage form is tablets, capsules and the like. The pharmaceutically-acceptable carriers suitable for the preparation of unit dosage forms for oral administration are well-known in the art. Their selection will depend on secondary considerations like taste, cost, and shelf stability, which are not critical for the purposes of the subject invention, and can be made without difficulty by those skilled in the art.

Methods of Use

The compounds of the present invention are useful in treating many medical disorders, including for example, ocular disorders, hypertension, fertility control, nasal congestion, neurogenic bladder disorder, gastrointestinal disorders, dermatological disorders, and osteoporosis.

The compounds of the present invention are useful in increasing (1) bone volume and trabecular number through formation of new trabeculae, (2) bone mass while maintaining a normalized bone turnover rate, and/or (3) formation at the endosteal surface without removing bone from the existing cortex. Thus, these compounds are useful in the treatment and prevention of bone disorders.

The preferred routes of administration for treating bone disorders are transdermal and intranasal. Other preferred routes of administration include rectal. sublingual, and oral.

The dosage range of the compound for systemic administration is from about 0.01 to about 1000 $\mu$g/kg body weight, preferably from about 0.1 to about 100 $\mu$g/kg per body weight, most preferably form about 1 to about 50 $\mu$g/kg body weight per day. The transdermal dosages will be designed to attain similar serum or plasma levels, based upon techniques known to those skilled in the art of pharmacokinetics and transdermal formulations. Plasma levels for systemic administration are expected to be in the range of 0.01 to 100 nanograms/mi, more preferably from 0.05 to 50 ng/ml, and most preferably from 0.1 to 10 ng/ml. While these dosages are based upon a daily administration rate, weekly or monthly accumulated dosages may also be used to calculate the clinical requirements.

Dosages may be varied based on the patient being treated, the condition being treated, the severity of the condition being treated, the route of administration, etc. to achieve the desired effect.

The compounds of the present invention are also useful in decreasing intraocular pressure. Thus, these compounds are useful in the treatment of glaucoma. The preferred route of administration for treating glaucoma is topically.

COMPOSITION AND METHOD EXAMPLES

The following non-limiting examples illustrate the subject invention. The following composition and method examples do not limit the invention, but provide guidance to the skilled artisan to prepare and use the compounds, compositions and methods of the invention. In each case other compounds within the invention may be substituted for the example compound shown below with similar results. The skilled practitioner will appreciate that the examples provide guidance and may be varied based on the condition being treated and the patient.

Example A

Pharmaceutical compositions in the form of tablets are prepared by conventional methods, such as mixing and direct compaction, formulated as follows:

| Ingredient | Quantity (mg per tablet) |
|---|---|
| Compound of Example 1 | 5 |
| Microcrystalline Cellulose | 100 |
| Sodium Starch Glycollate | 30 |
| Magnesium Stearate | 3 |

When administered orally once daily, the above composition substantially increases bone volume in a patient suffering from osteoporosis.

Example B

Pharmaceutical compositions in liquid form are prepared by conventional methods, formulated as follows:

| Ingredient | Quantity |
|---|---|
| Compound of Example 32 | 1 mg |
| Phosphate buffered physiological saline | 10 ml |
| Methyl Paraben | 0.05 ml |

When 1.0 ml of the above composition is administered subcutaneously once daily, the above composition substantially increases bone volume in a patient suffering from osteoporosis.

Example C

Topical pharmaceutical compositions for lowering intraocular pressure are prepared by conventional methods and formulated as follows:

| Ingredient | Amount (wt %) |
| --- | --- |
| Compound of Example 1 | 0.004 |
| Dextran 70 | 0.1 |
| Hydroxypropyl methylcellulose | 0.3 |
| Sodium Chloride | 0.77 |
| Potassium chloride | 0.12 |
| Disodium EDTA (Edetate disodium) | 0.05 |
| Benzalkonium chloride | 0.01 |
| HCL and/or NaOH | pH 7.2–7.5 |
| Purified water | q.s. to 100% |

While particular embodiments of the subject invention have been described, it would be obvious to those skilled in the art that various changes and modifications to the compositions disclosed herein can be made without departing from the spirit and scope of the invention. It is intended to cover, in the appended claims, all such modifications that are within the scope of this invention.

What is claimed is:

1. A compound having the structure:

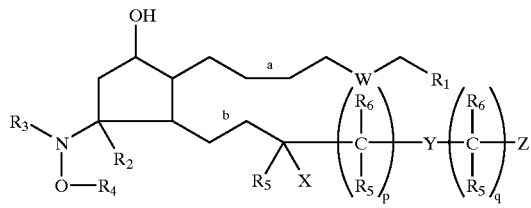

characterized in that
(a) $R_1$ is $CO_2H$, $C(O)NHOH$, $CO_2R_7$, $CH_2OH$, $S(O)_2R_7$, $C(O)NHR_7$, $C(O)NHS(O)_2R_7$, or tetrazole; characterized in that $R_7$ is alkyl, heteroalkyl, monocyclic carbocyclic aliphatic ring, monocyclic heterocyclic aliphatic ring, monocyclic aromatic ring, or monocyclic heteroaromatic ring;
(b) W is O, NH, S, S(O), S(O)$_2$, or (CH$_2$)$_m$; characterized in that m is an integer from 0 to about 3;
(c) $R_2$ is H and $R_3$ is H or lower alkyl, or $R_2$ and $R_3$ together form a covalent bond;
(d) $R_4$ is H, alkyl, heteroalkyl, monocyclic carbocyclic aliphatic ring, monocyclic heterocyclic aliphatic ring, monocyclic aromatic ring, or monocyclic heteroaromatic ring;
(e) each $R_5$ is independently selected from the group consisting of H, $CH_3$, and $C_2H_5$;
(f) X is $NHR_8$ or $OR_8$, characterized in that each $R_8$ is independently selected from the group consisting of H, acyl, alkyl, heteroalkyl, monocyclic carbocyclic aliphatic ring, monocyclic heterocyclic aliphatic ring, monocyclic aromatic ring, and monocyclic heteroaromatic ring;
(g) each $R_6$ is independently selected from the group consisting of H, $CH_3$, $C_2H_5$, $OR_8$, and $NHR_8$;
(h) Y is O, $NHR_8$, S, S(O), or S(O)$_2$, provided no carbon has more than one heteroatom attached to it;
(i) Z is H, methyl, monocyclic carbocyclic aliphatic ring, monocyclic heterocyclic aliphatic ring, monocyclic aromatic ring, monocyclic heteroaromatic ring, bicyclic carbocyclic aliphatic ring, bicyclic heterocyclic aliphatic ring, bicyclic aromatic ring, or bicyclic heteroaromatic ring, provided that when Y is S, S(O), or S(O)$_2$ and Z is H, q is at least 1;
(j) a and b are independently selected from the group consisting of single bond, cis double bond, and trans double bond;
(k) p is an integer from 1 to 5, q is an integer from 0 to 5, and p+q is 1 to 5; and
any optical isomer, diastereomer, enantiomer of the above structure or a pharmaceutically-acceptable salt, or bio-hydrolyzable amide, ester, or imide thereof.

2. The compound of claim 1 wherein $R_1$ is $CO_2H$, $C(O)NHOH$, $CO_2R_7$, $C(O)NHS(O)_2R_7$, or tetrazole.
3. The compound of claim 2 wherein W is O or (CH$_2$)$_m$.
4. The compound of claim 3 wherein $R_4$ and $R_5$ are each H and X is OH.
5. The compound of claim 4 wherein $R_1$ is $CO_2H$ or $CO_2R_7$.
6. The compound of claim 5 wherein W is (CH$_2$)$_1$.
7. The compound of claim 6 wherein p+q is 1 or 2.
8. The compound of claim 7 wherein Z is monocyclic aromatic ring or monocyclic heteroaromatic ring.
9. The compound of claim 6 wherein p+q is 3 to 5.
10. The compound of claim 9 wherein Z is H or methyl.
11. The compound of claim 8 wherein a is a cis double bond and b is a trans double bond.
12. The compound of claim 10 wherein a is a cis double bond and b is a trans double bond.
13. The compound of claim 11 wherein $R_2$ and $R_3$ are both H.
14. The compound of claim 11 wherein $R_2$ and $R_3$ together form a double bond.
15. The compound of claim 12 wherein $R_2$ and $R_3$ are both H.
16. The compound of claim 12 wherein $R_2$ and $R_3$ together form a double bond.
17. A method of treating a human or other animal subject having a bone disorder, said method comprising administering to said subject a compound according to the structure:

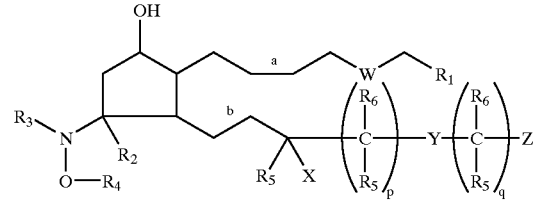

wherein
(a) $R_1$ is $CO_2H$, $C(O)NHOH$, $CO_2R_7$, $CH_2OH$, $S(O)_2R_7$, $C(O)NHR_7$, $C(O)NHS(O)_2R_7$, or tetrazole; wherein $R_7$ is alkyl, heteroalkyl, monocyclic carbocyclic aliphatic ring, monocyclic heterocyclic aliphatic ring, monocyclic aromatic ring, or monocyclic heteroaromatic ring;
(b) W is O, NH, S, S(O), S(O)$_2$, or (CH$_2$)$_m$; wherein m is an integer from 0 to about 3;
(c) $R_2$ is H and $R_3$ is H or lower alkyl, or $R_2$ and $R_3$ together form a covalent bond;
(d) $R_4$ is H, alkyl, heteroalkyl, monocyclic carbocyclic aliphatic ring, monocyclic heterocyclic aliphatic ring, monocyclic aromatic ring, or monocyclic heteroaromatic ring;
(e) each $R_5$ is independently selected from the group consisting of H, $CH_3$, and $C_2H_5$;
(f) X is $NHR_8$ or $OR_8$, wherein each $R_8$ is independently selected from the group consisting of H, acyl, alkyl, heteroalkyl, monocyclic carbocyclic aliphatic ring, monocyclic heterocyclic aliphatic ring, monocyclic aromatic ring, and monocyclic heteroaromatic ring;
(g) each $R_6$ is independently selected from the group consisting of H, $CH_3$, $C_2H_5$, $OR_8$, and $NHR_8$;
(h) Y is O, $NHR_8$, S, S(O), or $S(O)_2$, provided no carbon has more than one heteroatom attached to it;
(i) Z is H, methyl, monocyclic carbocyclic aliphatic ring, monocyclic heterocyclic aliphatic ring, monocyclic aromatic ring, monocyclic heteroaromatic ring, bicyclic carbocyclic aliphatic ring, bicyclic heterocyclic aliphatic ring, bicyclic aromatic ring, or bicyclic heteroaromatic ring, provided that when Y is S, S(O), or $S(O)_2$ and Z is H, q is at least 1;
(j) a and b are independently selected from the group consisting of single bond, cis double bond, and trans double bond;
(k) p is an integer from 1 to 5, q is an integer from 0 to 5, and p+q is 1 to 5; and
any optical isomer, diastereomer, enantiomer of the above structure or a pharmaceutically-acceptable salt, or bio-hydrolyzable amide, ester, or imide thereof.

18. The method of claim 17 wherein said disorder is osteoporosis.

19. The method of claim 18 wherein in osteoporosis is post-menopausal.

20. The method of claim 18 wherein in osteoporosis is cortico-steroid induced.

21. The method of claim 17 wherein said bone disorder is osteopenia.

22. The method of claim 17 wherein said bone disorder is a bone fracture.

23. The method of claim 17 wherein said compound is administered orally.

24. The method of claim 17 wherein said compound is administered transdermally.

25. The method of claim 17 wherein said compound is administered intranasally.

26. A method of treating glaucoma, said method comprising administering to a human or other animal a safe and effective amount of a compound according to the structure:

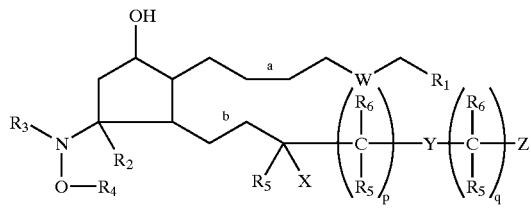

wherein
(a) $R_1$ is $CO_2H$, C(O)NHOH, $CO_2R_7$, $CH_2OH$, $S(O)_2R_7$, $C(O)NHR_7$, $C(O)NHS(O)_2R_7$, or tetrazoie; wherein $R_7$ is alkyl, heteroalkyl, monocyclic carbocyclic aliphatic ring, monocyclic heterocyclic aliphatic ring, monocyclic aromatic ring, or monocyclic heteroaromatic ring;
(b) W is O, NH, S, S(O), $S(O)_2$, or $(CH_2)_m$; wherein m is an integer from 0 to about 3;
(c) $R_2$ is H and $R_3$ is H or lower alkyl, or $R_2$ and $R_3$ together form a covalent bond;
(d) $R_4$ is H, alkyl, heteroalkyl, monocyclic carbocyclic aliphatic ring, monocyclic heterocyclic aliphatic ring, monocyclic aromatic ring, or monocyclic heteroaromatic ring;
(e) each $R_5$ is independently selected from the group consisting of H, $CH_3$, and $C_2H_5$;
(f) X is $NHR_8$ or $OR_8$, wherein each $R_8$ is independently selected from the group consisting of H, acyl, alkyl, heteroalkyl, monocyclic carbocyclic aliphatic ring, monocyclic heterocyclic aliphatic ring, monocyclic aromatic ring, and monocyclic heteroaromatic ring;
(g) each $R_6$ is independently selected from the group consisting of H, $CH_3$, $C_2H_5$, $OR_8$, and $NHR_8$;
(h) Y is O, $NHR_8$, S, S(O), or $S(O)_2$, provided no carbon has more than one heteroatom attached to it;
(i) Z is H, methyl, monocyclic carbocyclic aliphatic ring, monocyclic heterocyclic aliphatic ring, monocyclic aromatic ring, monocyclic heteroaromatic ring, bicyclic carbocyclic aliphatic ring, bicyclic heterocyclic aliphatic ring, bicyclic aromatic ring, or bicyclic heteroaromatic ring, provided that when Y is S, S(O), or $S(O)_2$ and Z is H, q is at least 1;
(j) a and b are independently selected from the group consisting of single bond, cis double bond, and trans double bond;
(k) p is an integer from 1 to 5, q is an integer from 0 to 5, and p+q is 1 to 5; and
any optical isomer, diastereomer, enantiomer of the above structure or a pharmaceutically-acceptable salt, or bio-hydrolyzable amide, ester, or imide thereof.

27. The method of claim 26 wherein said compound is administered topically.

* * * * *

UNITED STATES PATENT AND TRADEMARK OFFICE
CERTIFICATE OF CORRECTION

PATENT NO.    : 6,444,840 B1
DATED         : September 3, 2002
INVENTOR(S)   : deLong et al.

It is certified that error appears in the above-identified patent and that said Letters Patent is hereby corrected as shown below:

Column 4,
Line 15, please delete "I" and insert -- 1 --.

Column 9,
Line 3, please delete "7" and insert -- 7- --.

Column 14,
Structure S2g, please delete " " and insert -- --.

Column 16,
Structure S2k, please delete " " and insert -- --.

Column 22,
Structure 1h, please delete " $\xrightarrow{\text{NH2OH}}_{\text{NaOAc}}$ " and insert -- $\xrightarrow{\text{NH}_2\text{OH}}_{\text{NaOAc}}$ --.

Column 29,
Line 39, delete "Benzoyfoxy" and insert -- Benzoyloxy --.

Column 30,
Structure 16f, please delete "OMe" and insert -- $CO_2Me$ --.

Signed and Sealed this

Twentieth Day of July, 2004

JON W. DUDAS
*Acting Director of the United States Patent and Trademark Office*